United States Patent
Schober et al.

(10) Patent No.: US 10,376,392 B2
(45) Date of Patent: Aug. 13, 2019

(54) PROSTHETIC SOCKET SEALING SYSTEM AND METHOD

(71) Applicant: The Ohio Willow Wood Company, Mount Sterling, OH (US)

(72) Inventors: Glenn R. Schober, Tipp City, OH (US); John P. Jones, Cambden, OH (US); Mark W. Groves, Columbus, OH (US); Christopher T. Kelley, Grandview Heights, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 66 days.

(21) Appl. No.: 15/620,981

(22) Filed: Jun. 13, 2017

(65) Prior Publication Data

US 2017/0281373 A1    Oct. 5, 2017

Related U.S. Application Data

(62) Division of application No. 14/979,956, filed on Dec. 28, 2015, now abandoned, which is a division of application No. 14/111,682, filed as application No. PCT/US2012/033855 on Apr. 16, 2012, now abandoned.

(51) Int. Cl.
*A61F 2/78* (2006.01)
*A61F 2/80* (2006.01)

(52) U.S. Cl.
CPC .............. *A61F 2/80* (2013.01); *A61F 2/7812* (2013.01); *A61F 2002/7837* (2013.01); *A61F 2002/802* (2013.01); *A61F 2002/805* (2013.01)

(58) Field of Classification Search
CPC ........ A61F 2/5044; A61F 2/5046; A61F 2/78; A61F 2/7812; A61F 2/80; A61F 2002/5052; A61F 2002/805; A61F 2002/807

See application file for complete search history.

(56) References Cited

U.S. PATENT DOCUMENTS 2,002,064 A  *  5/1935  Kohl ................ A61F 2/7843
                                                    623/36
2004/0098136 A1 *  5/2004 Caspers ............ A61F 2/5046
                                                    623/34

OTHER PUBLICATIONS

Sutton, Erin. Successful incorporation of engineers into patient care: a case report. Apr. 2012. O&P Edge Magazine.*

* cited by examiner

*Primary Examiner* — Christie L Bahena
(74) *Attorney, Agent, or Firm* — Benesch Friedlander Coplan & Aronoff LLP

(57) ABSTRACT

Prosthetic socket sealing systems and methods of use. Embodiments of the present invention include various combinations of sealing elements that are associated with a rigid prosthetic socket and act to seal the socket interior against air intrusion or escape via the open proximal end thereof. The socket interior may thus be evacuated for purposes of vacuum suspension or otherwise.

6 Claims, 19 Drawing Sheets

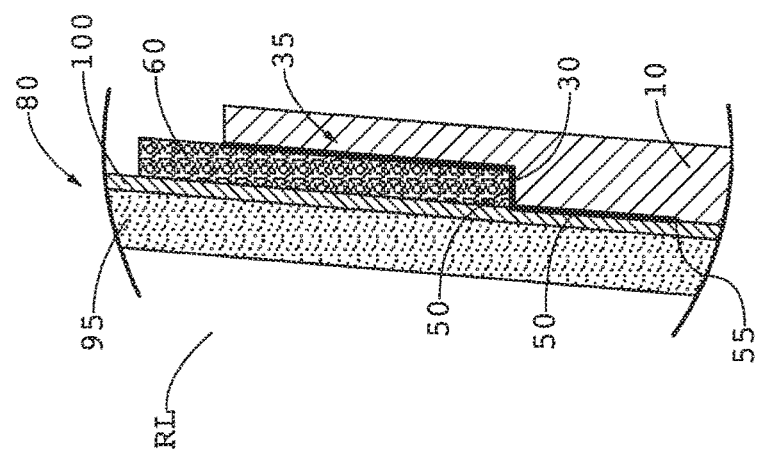
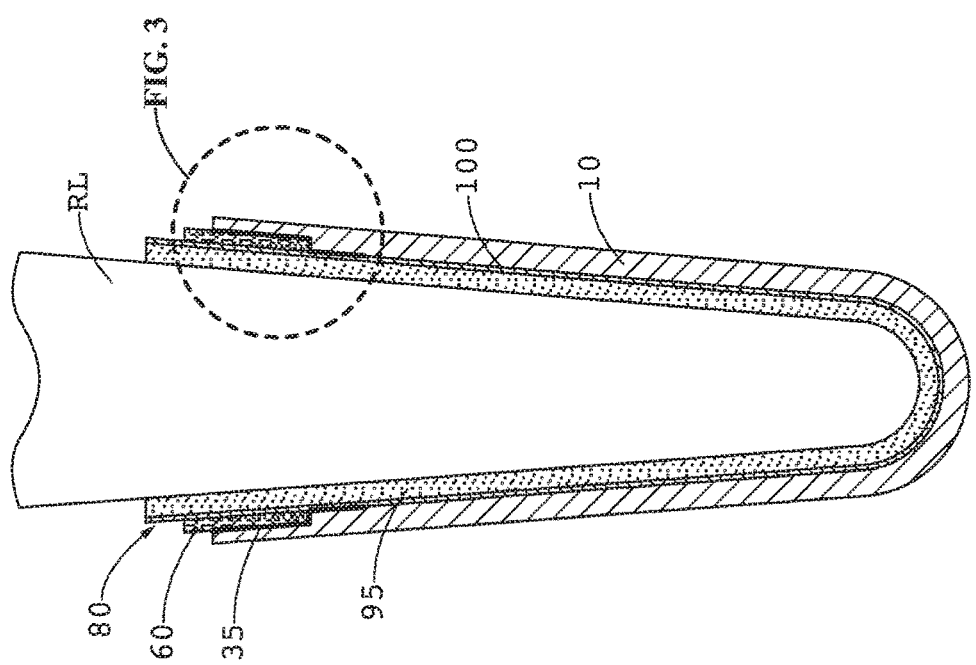

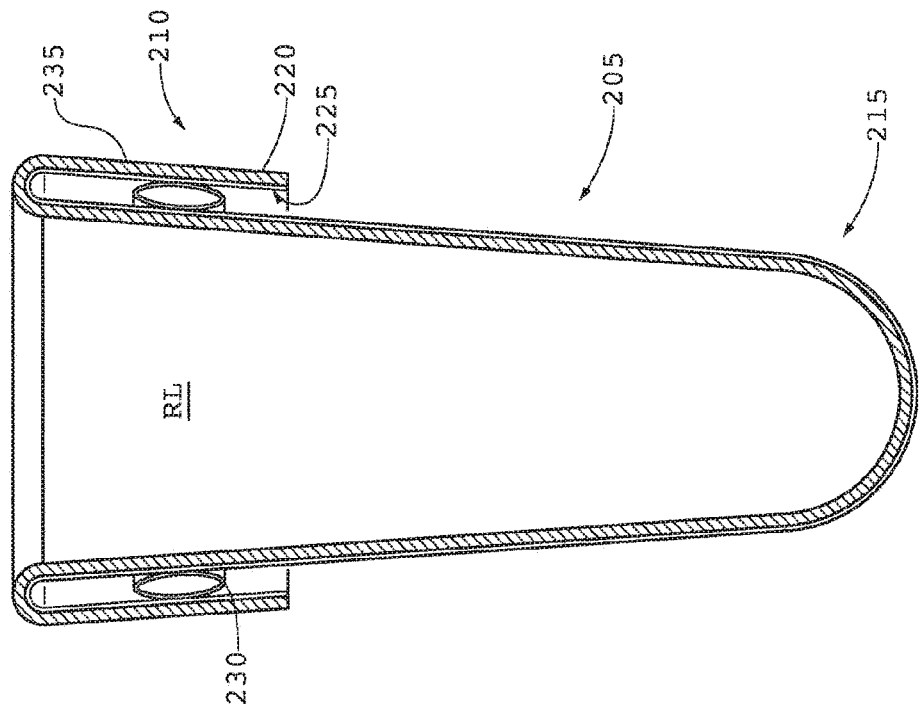
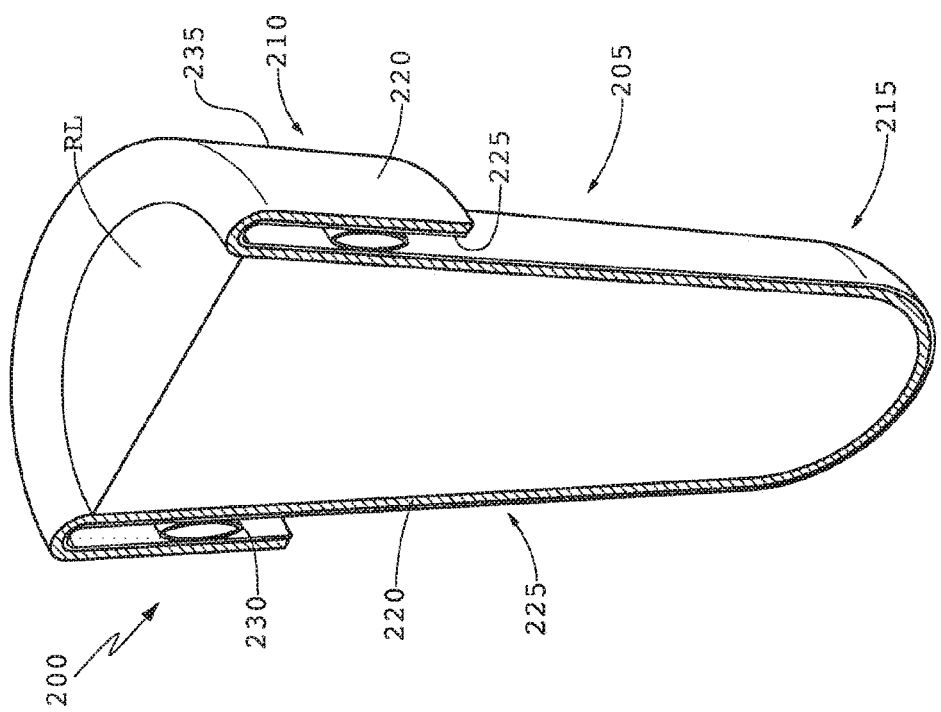

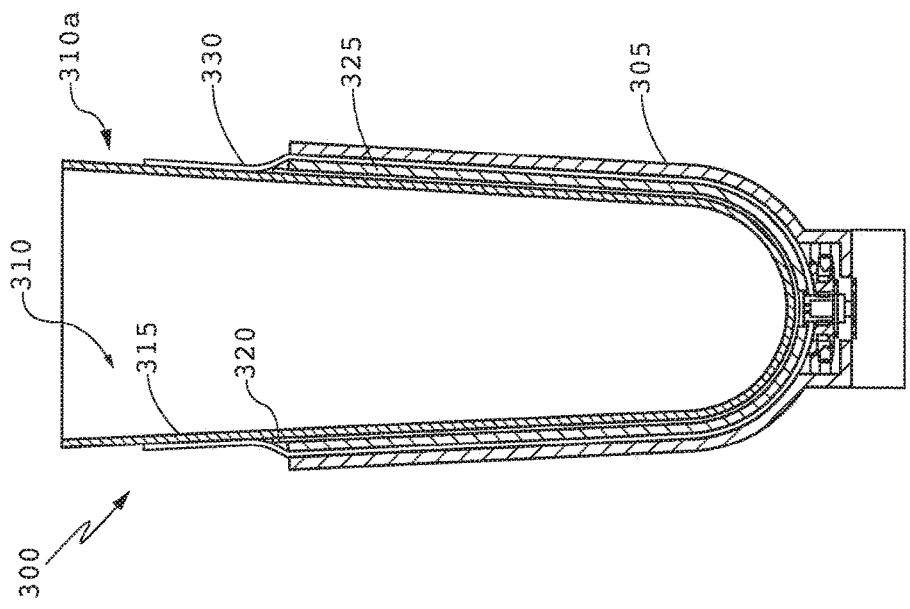
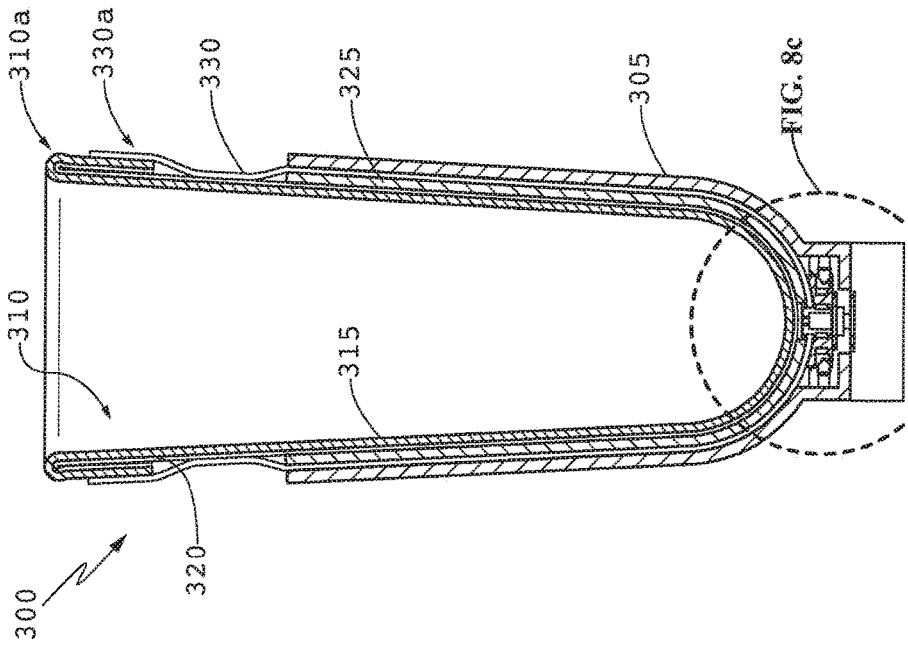

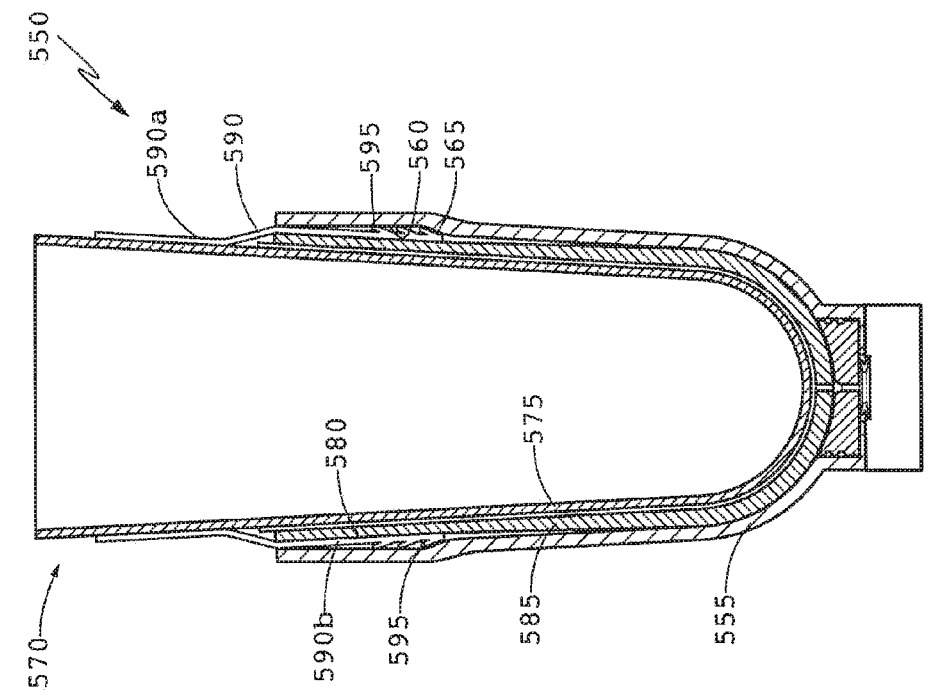
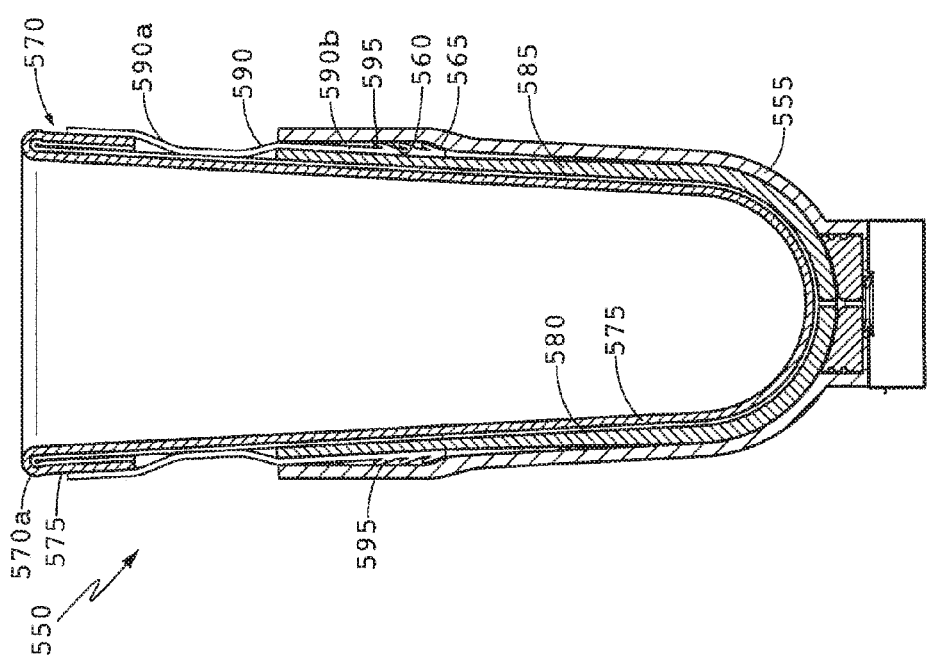

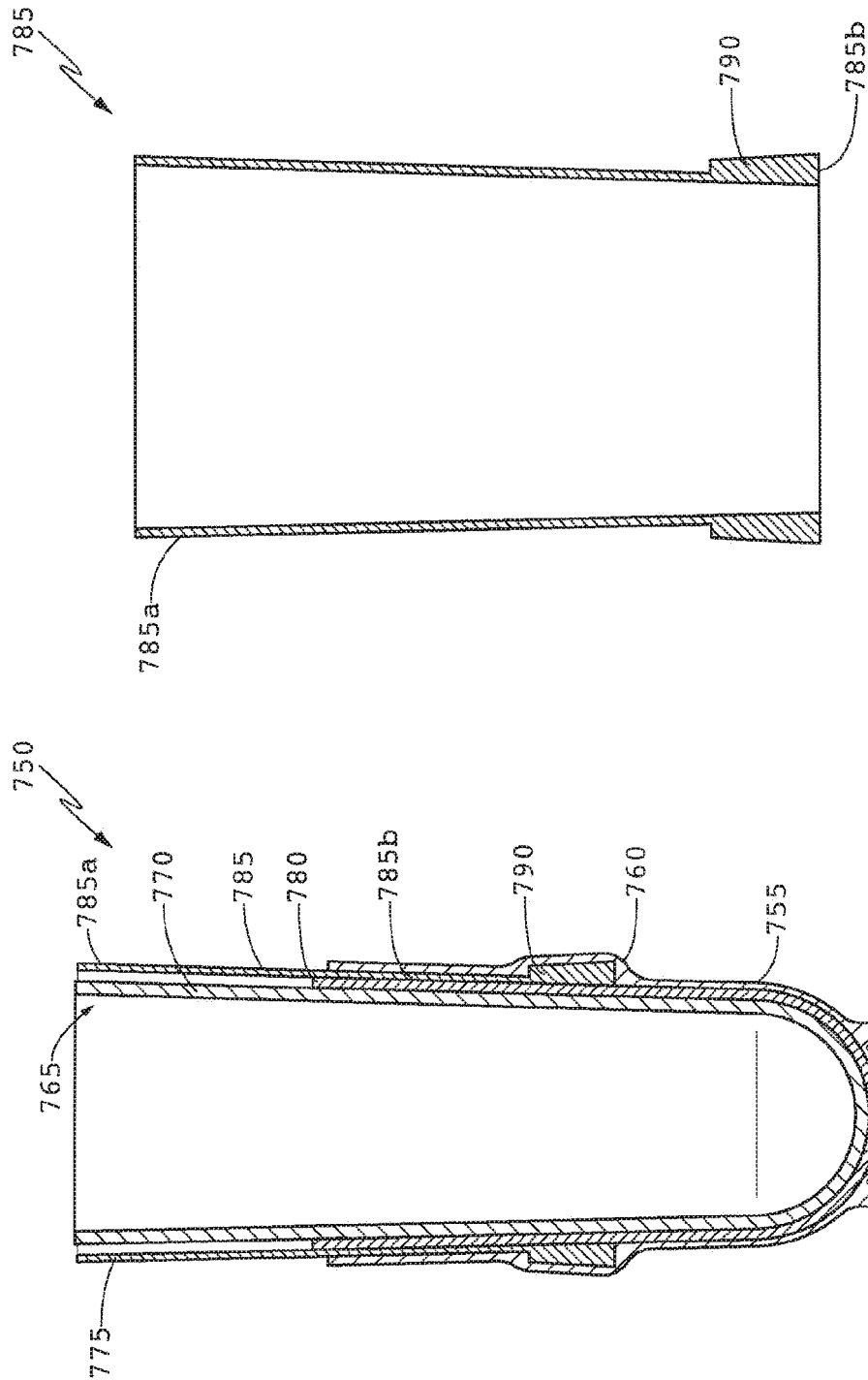

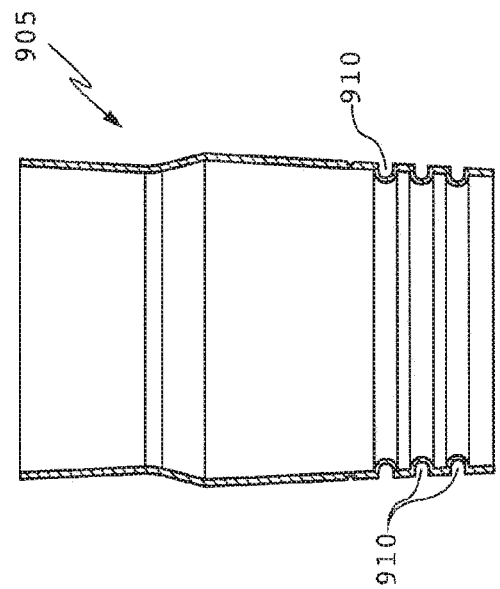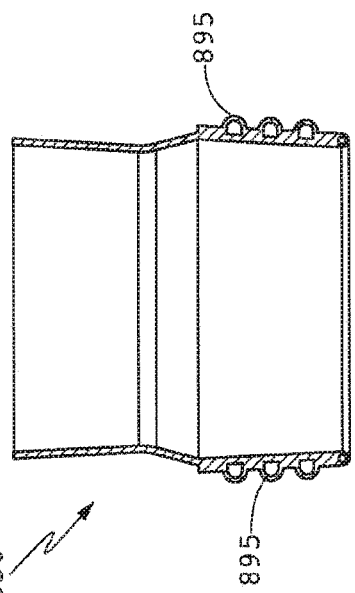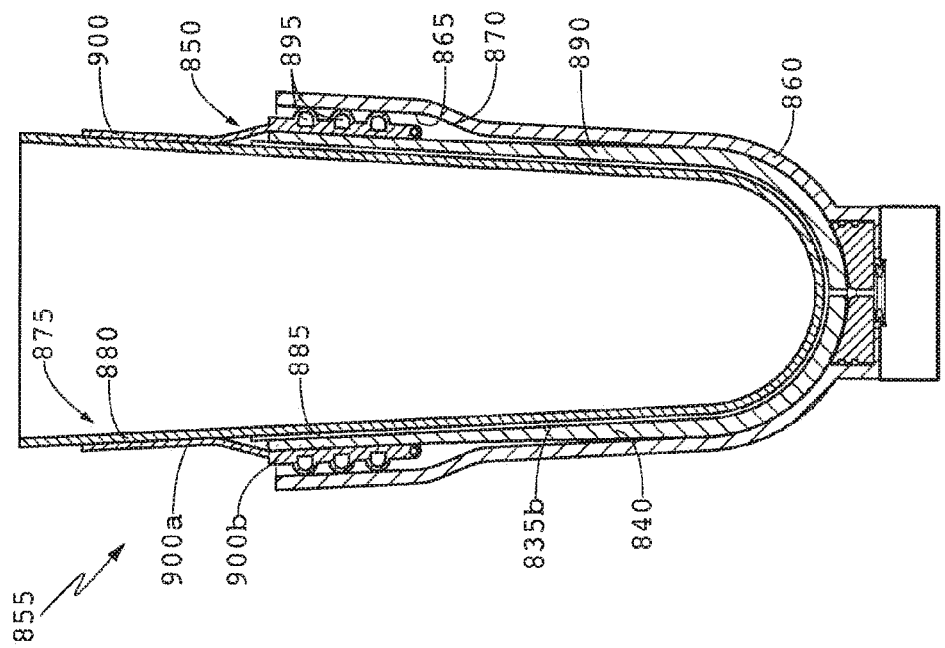

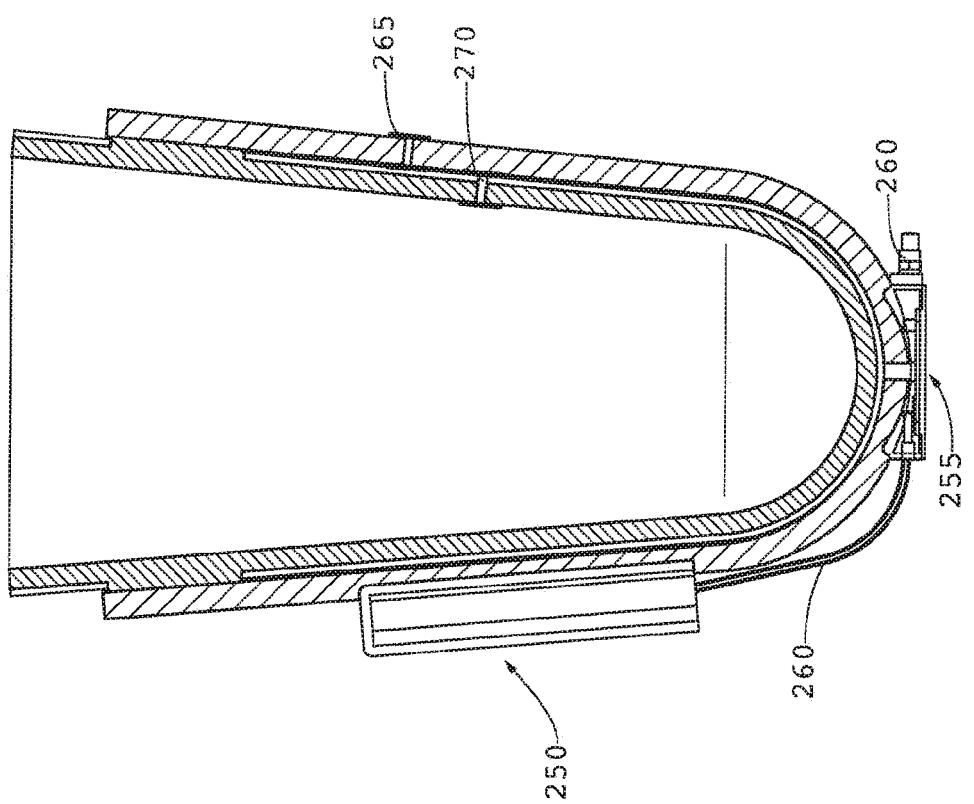

PROSTHETIC SOCKET SEALING SYSTEM AND METHOD

RELATED APPLICATIONS

This application is a divisional of U.S. patent application Ser. No. 14/979,956, filed on Dec. 28, 2015, which is a divisional of U.S. patent application Ser. No. 14/111,682, filed Nov. 5, 2013, which claims priority from International Application No. PCT/US2012/033855, filed Apr. 16, 2012, and from provisional U.S. Patent Application 61/475,599, filed Apr. 14, 2011, each of which is incorporated by reference in its entirety.

TECHNICAL FIELD

The present invention is directed to a sealing system and sealing method for a prosthetic socket, and also to prosthetic vacuum suspension.

BACKGROUND

In prosthetics, an amputee normally dons a prosthetic device by inserting his/her residual limb into a socket portion of the prosthesis. It is now fairly typical for an amputee to first place a prosthetic liner over the residual limb prior to insertion of the residual limb into the prosthetic socket, the prosthetic liner acting at least as a cushioning interface between the limb and socket. The Alpha® Liner series of prosthetic liners from the Ohio Willow Wood Company in Mt. Sterling, Ohio has proven to be quite popular for this purpose.

Regardless of the selected limb preparation, the prosthesis must be securely retained on the residual limb in order to permit proper prosthesis function and amputee comfort. Various techniques for prosthesis retention (suspension) have been utilized over the years, and these techniques would be well known to one of skill in the art. Two suspension techniques that have become increasingly popular—especially since the advent of modem prosthetic liners—are locking (e.g., pin lock) suspension and vacuum (suction) suspension.

In the case of locking suspension, a pin or similar element is typically secured to the distal end of a prosthetic liner and a corresponding pin-receiving lock element is located in a distal end of a prosthetic socket. Upon insertion of the liner-covered residual limb into the socket, engagement of the pin and lock element serves to retain the associated prosthesis on the residual limb. In the case of vacuum suspension, a typically liner-covered residual limb is inserted into a prosthetic socket. A suspension sleeve may also be placed over the brim portion of the socket so as to overlie both the socket exterior and a portion of the residual limb (or liner). In this manner, air may be prevented from entering or exiting the socket from the proximal end thereof, thereby facilitating the creation and maintenance of a vacuum within the socket. A vacuum device can then be used to evacuate the socket interior to some desired vacuum level, the force of the vacuum holding the prosthetic socket (and prosthesis) on the residual limb.

Obviously, the ability to generate and maintain a vacuum is critical in the case of prosthetic vacuum suspension. If an adequate vacuum level cannot be produced within the socket, the associated prosthesis will not be properly secured to the residual limb. If vacuum is lost during use of the prosthesis, the prosthesis may become loose leading to possible discomfort or malfunction. Adequately sealing a prosthetic socket can be difficult even in the case of a below-knee, i.e., trans-tibial, (TT) amputee. However, these difficulties are often compounded in the case of an above-knee, i.e., trans-femoral (TF) amputee.

More specifically, while there are known and effective vacuum suspension solutions for TT amputees, no similarly effective vacuum solutions have been developed for TF amputees. Rather, the most common TT socket sealing solution is to place a suspension (sealing) sleeve over the outside of the socket and the liner covering the wearer's thigh. However, since TF sockets do not have sufficient room above the brim of the socket for sealing to the liner, the liner must be reflected over the brim of the socket and then sealed to the socket with a sleeve. This technique is not very durable because amputees commonly bump the brim of the socket against hard objects, which may damage the liner and/or the sleeve. Furthermore, the presence of a bulky sealing sleeve near or in the groin area may be quite uncomfortable to an amputee.

Internal sealing systems have been developed for TF prostheses, but all known systems have unacceptable drawbacks. These drawbacks include, without limitation: that the seal requires an intimate fit to the residual limb and will not be effective if the limb shrinks or moves in such a way as to break the seal; that the seal resides too low within the socket, and resulting vacuum suspension is thereby concentrated over too small of an area of the residual limb; and that the sealing element is too restrictive and must be fit very carefully to avoid a constricting "tourniquet effect" on the residual limb.

Therefore, it can be understood from the foregoing discussion that there is a need for an improved vacuum suspension sealing system, especially an improved vacuum suspension sealing system for a TF prosthesis. Sealing systems and methods of the present invention satisfy these needs.

SUMMARY OF THE OF THE GENERAL INVENTIVE CONCEPT

Socket sealing systems of the present invention include an internal socket seal that may work with a residual limb or with a prosthetic liner to effectively seal the socket against air (vacuum) leaks. The benefit to an amputee is a more comfortable and durable liner/socket system that maintains its fit during a wide range of activities and during physical changes (e.g., swelling or shrinkage) to the residual limb.

One exemplary embodiment of a socket sealing system of the present invention generally includes at least a specially designed or modified prosthetic socket, a flexible internal seal (membrane) for sealing the socket to a residual limb (or liner), and an inner brim element that secures the inner membrane to the socket interior. Such an embodiment may further include an optional prosthetic liner for donning over an amputee's residual limb, an optional vacuum system, an optional bypass valve, and an optional release valve.

In this embodiment of the socket sealing system, the sealing membrane is preferably a thin-walled elastomeric band that includes a first (proximal) end and a second (distal). The opening at the proximal end may be larger than the opening at the second end. In any event, the distal opening is preferably of a dimension that is less than a corresponding dimension of an amputee's residual limb, such that the membrane seals against the residual limb (or a liner) when the limb is passed through the membrane. The proximal end of the sealing membrane fits (typically by stretching) over the distal end of the inner brim, and the distal end of the sealing membrane preferably extends below the distal edge of the inner brim when in use.

After installation of the sealing membrane to the inner brim, the inner brim/sealing membrane assembly is then inserted into the prosthetic socket so that the sealing membrane is partially sandwiched between an interior portion of the prosthetic socket and a corresponding exterior portion of the inner brim, thereby securing and sealing the membrane against the socket. The amputee's residual limb may then be inserted into the socket. When the residual limb resides within the socket, the distal opening in the sealing membrane will conform to the exterior surface of the residual limb and seal either directly against the skin of the residual limb or against a prosthetic liner that covers the residual limb. The flexible nature of the membrane allows the seal between the residual limb and the membrane to be maintained even if the residual limb moves within the socket or undergoes a change in shape.

As a result, the interior of the prosthetic socket is sealed—meaning that air is prevented from entering or exiting the socket from the proximal end thereof. Consequently, the socket interior may be evacuated for the purpose of vacuum suspension of a prosthesis or for other reasons, and an acceptable level of vacuum may be maintained during wearing of the prosthesis.

Another exemplary embodiment of a socket sealing system of the present invention generally includes at least a prosthetic liner for donning over an amputee's residual limb, and an inflatable elastomeric sealing ring for sealing a portion of the prosthetic liner against an interior wall of a socket. Such an embodiment may further include an optional vacuum system, an optional bypass valve, and an optional release valve.

This embodiment of a socket sealing system may use substantially any standard prosthetic socket. The inflatable elastomeric sealing ring is generally thin-walled and may be substantially round or oval in cross-section. When the sealing ring is inflated, the central opening of the sealing ring is preferably smaller than the external periphery of the residual limb that will be inserted into the socket so that the sealing ring will fit snugly on the residual limb.

To use this embodiment of the sealing system, an amputee first dons a prosthetic liner, then slides the sealing ring over the exterior of the liner to a point near the proximal (open) end thereof. The proximal end of the liner is then reflected over the sealing ring such that the sealing ring is sandwiched between the reflected portion of the liner and a portion of the liner that resides against the residual limb. The liner-covered residual limb with the sealing ring is then inserted into the prosthetic socket so that the sealing ring resides within the socket.

With the liner-covered residual limb and the sealing ring inserted into the socket, air is then evacuated from the socket interior. As the socket is evacuated, the sealing ring will expand, further pressing the reflected proximal end of the liner against the inside wall of the socket. This seals the liner against the socket interior, thereby also sealing the socket interior such that air is prevented from entering or exiting the socket from the proximal end thereof. Consequently, the socket interior may be evacuated for the purpose of vacuum suspension or otherwise, and an acceptable level of vacuum may be maintained during wearing of the prosthesis.

Variations of this exemplary embodiment are also possible. For example, an inflatable sealing ring could be incorporated into or onto a liner, thereby eliminating the need for the liner to be reflected over the sealing ring at the proximal end. In this variation, the inflatable sealing ring would be adapted to seal against the interior wall of a socket.

In another variation, it may be possible to attach an inflatable sealing ring to the interior wall of a socket, such that a seal is created between the sealing ring and the socket wall. This would also eliminate the need for the liner to be reflected over the sealing ring at the proximal end. In this variation, the inflatable sealing ring would be adapted to seal against the skin of a residual limb or the exterior of a liner. In the latter case, the liner may also be adapted to facilitate a seal with the sealing ring. In this variation, it may also be possible to pass a valve stem or similar element from the inflatable sealing ring through the socket wall, such that the volume of air or other gas in the sealing ring may be adjusted.

Yet another embodiment of the present invention may combine elements of the first and second exemplary embodiments described above. More particularly, an inflatable sealing ring may be attached to an inner brim element and located in a prosthetic socket upon insertion of the inner brim. In this variation, the inflatable sealing ring would again be adapted to seal against the skin of a residual limb or the exterior of a liner.

Another exemplary embodiment of a socket sealing system of the present invention generally includes a rigid prosthetic socket; a prosthetic liner, such as a polymeric prosthetic liner with a fabric-covered exterior, for donning over an amputee's residual limb; a soft inner socket for receiving a portion of the liner-covered residual limb; and a polymeric sealing sleeve (which may have a partially fabric-covered exterior) having a closed end that is pulled over and seals against the soft inner socket. The combination of the prosthetic liner, soft inner socket and sealing sleeve are placed on a residual limb and the residual limb is thereafter inserted into the rigid prosthetic socket. The proximal open end of the sealing sleeve extends beyond the open ends of the soft and rigid sockets to contact and seal against a reflected proximal end of the prosthetic liner, which also extends beyond the open ends of the soft and rigid sockets.

In a variation of this embodiment, the fabric covering on the exterior of the prosthetic liner may terminate at some point before reaching the proximal open end of the liner, or a section of the fabric covering may be removed, thus leaving a circumferential band of exposed polymeric material along a portion of the liner that extends beyond the soft and rigid sockets. In this case, the liner is not reflected. Rather, the polymeric material interior of the sealing sleeve contacts and seals against the exposed polymeric material of the liner.

Another exemplary embodiment of a socket sealing system of the present invention generally includes a prosthetic liner, such as a polymeric prosthetic liner with a fabric-covered exterior, for donning over an amputee's residual limb; a rigid prosthetic socket having an area of relief along the interior of its proximal end that results in a peripheral shoulder within the socket; a ring-like inner brim component of regular or irregular peripheral shape that is designed to reside in the relief area of the rigid socket; and an open-ended polymeric sealing sleeve (which may have a partially fabric-covered exterior), a distal portion of which is designed to reside within the relief area of the rigid socket and to overlie and seal against the brim component, and a proximal portion of which is designed to extend from the rigid socket and to seal against a portion of the prosthetic liner (or residual limb) that also extends from the rigid socket.

As with the previously described embodiment, the proximal open end of the liner may be reflected, such that the polymeric material interior at the proximal end of the sealing sleeve contacts and seals against the exposed polymeric material of the reflected liner. Alternatively, the fabric covering on the exterior of the prosthetic liner may terminate at some point before reaching the open end thereof, or a section of the fabric covering may be removed, thus leaving a circumferential band of exposed polymeric material along a portion of the liner that extends beyond the soft and rigid sockets. In this case, the liner is not reflected. Rather, the polymeric material interior of the sealing sleeve contacts and seals against the exposed polymeric material of the liner.

In another embodiment of the invention, the brim component of the just described embodiment may be replaced with one or a plurality of substantially solid sealing elements that are an integral part of and extend from the open-ended sealing sleeve in the area thereof that resides within the relief area at the proximal end of the rigid prosthetic socket. The sealing elements may be, for example, one or a plurality of variously shaped protuberances that extend circumferentially around the exterior of the sealing sleeve. The sealing elements are preferably devoid of a fabric covering so as to better seal against the interior of the rigid prosthetic socket. Sealing of the prosthetic liner to the sealing sleeve according to this variation may again be facilitated by reflecting the proximal open end of the liner or exposing a section of the polymeric material thereof, as is described above.

Another exemplary embodiment of a socket sealing system of the present invention is similar to the embodiments described immediately above. Thus, this embodiment generally includes a prosthetic liner, such as a polymeric prosthetic liner with a fabric-covered exterior, for donning over an amputee's residual limb; a rigid prosthetic (outer) socket having an area of relief along the interior of its proximal end that results in a peripheral shoulder within the socket; and an open-ended polymeric sealing sleeve (which may have a partially fabric-covered exterior), a distal portion of which is designed to reside within the relief area of the rigid socket, and a proximal portion of which is designed to extend from the rigid socket and to seal against a portion of the prosthetic liner that also extends from the rigid socket. The sealing Sleeve again includes one or a plurality of sealing elements that are an integral part of and extend from the sealing sleeve in the area thereof that resides Within the relief area at the proximal end of the rigid socket. The sealing elements may again be one or a plurality of variously shaped protuberances that extend circumferentially around the exterior of the sealing sleeve and are preferably devoid of a fabric covering so as to better seal against the interior of the prosthetic socket.

In addition to these elements, this exemplary embodiment further includes a soft inner socket for receiving a portion of the liner-covered residual limb. The soft inner socket resides between the prosthetic liner and the sealing sleeve, such that a portion of sealing sleeve overlies and seals against a portion of the soft inner socket in the relief area of the rigid outer socket. Sealing of the prosthetic liner to the sealing sleeve according to this variation may again be accomplished by reflecting the proximal open end of the liner or exposing a section of the polymeric material thereof, as is described above.

In a variation of the previous embodiment, the plurality of sealing elements described as being an integral part of and extending from the open-ended sealing sleeve, are instead part of a separate component. More specifically, this variation includes a separate sealing band that includes the sealing elements and is designed to encircle and seal against the soft inner socket and to reside between the soft inner socket and the rigid outer socket in the relief area of the rigid socket. The sealing elements may again be, for example, one or a plurality of variously shaped protuberances that extend circumferentially around the exterior of the sealing band and are preferably devoid of a fabric covering so as to better seal against the interior of the prosthetic socket.

The sealing band is employed to provide a seal between the soft inner socket and the rigid outer socket, and resides distally of the sealing sleeve, which is still present and still includes a portion that resides within the relief section of the rigid outer socket. The sealing sleeve functions as described above with respect to sealing against the prosthetic liner which may again be reflected or provided with an area of exposed polymeric material.

Another embodiment again includes a prosthetic liner, such as a polymeric prosthetic liner with a fabric-covered exterior, for donning over an amputee's residual limb; a rigid prosthetic (outer) socket having an area of relief along the interior of its proximal end that results in a peripheral shoulder within the socket; and an open-ended polymeric sealing sleeve (which may have a partially fabric-covered exterior), a distal portion of which is designed to reside within the relief area of the rigid socket, and a proximal portion of which is designed to extend from the rigid socket and to seal against a portion of the prosthetic liner that also extends from the rigid socket. The sealing sleeve again includes one or a plurality of sealing elements that are an integral part of and extend from the sealing sleeve in the area thereof that resides within the relief area at the proximal end of the rigid socket. The sealing elements may again be one or a plurality of variously shaped protuberances that extend circumferentially around the exterior of the sealing sleeve and are preferably devoid of a fabric covering so as to better seal against the interior of the prosthetic socket.

In this embodiment, the soft inner socket is replaced by a ring-like inner brim component of regular or irregular peripheral shape that is designed to reside in the relief area of the rigid outer socket between the prosthetic liner and the sealing ring and portion of the sealing sleeve that resides in the relief area of the rigid outer socket. The interior of the sealing sleeve seals against the outer surface of the inner brim component, and the sealing sleeve otherwise functions as described above with respect to sealing against the prosthetic liner—which again may be reflected or provided with an area of exposed polymeric material as described above.

In a variation of this embodiment, the single sealing sleeve having sealing elements as an integral part thereof is replaced with a separate sealing sleeve and sealing band. Consequently, in this embodiment, the sealing band includes the sealing elements and is designed to encircle and seal against the soft inner socket and to reside between the soft inner socket and the rigid outer socket in the relief area of the rigid outer socket. The sealing elements may again be one or a plurality of variously shaped protuberances that extend circumferentially around the exterior of the sealing band and are preferably devoid of a fabric covering so as to better seal against the interior of the prosthetic socket.

The seating band is employed to provide a seal between the soft inner socket and the rigid outer socket, and resides distally of the sealing sleeve, which is still present and still includes a portion that resides within the relief section of the rigid outer socket. The sealing sleeve functions as described above with respect to sealing against the prosthetic liner—which may again be reflected or provided with an area of exposed polymeric material.

In any of the aforementioned embodiments having a sealing sleeve or sealing band with one or more encircling sealing elements that are an integral part thereof, the substantially solid sealing elements may be replaced with one or more gas-filled bladders. The bladders may be provided in a number of shapes. The sealing elements are again preferably devoid of a fabric covering so as to better seal against the interior of the prosthetic socket. In this case, sealing is assisted by the natural inflation of the bladders resulting from evacuation of the rigid outer socket.

In any of the aforementioned embodiments having a soft inner socket or an inner brim component, the proximal terminus thereof may, but is not necessarily required to, occur at approximately the same location as the proximal terminus of the rigid outer socket. Alternatively, it may be possible for one of the soft inner socket or inner brim component to extend proximally farther then the rigid outer socket, or vice versa.

Another exemplary embodiment of a socket sealing system of the present invention again generally includes a prosthetic liner, such as a polymeric prosthetic liner with a fabric-covered exterior, for donning over an amputee's residual limb; a soft inner socket for receiving a portion of the liner—covered residual limb; and an open-ended polymeric sealing sleeve (which may have a partially fabric-covered exterior) having a distal portion that overlies the soft inner socket. This embodiment also includes a rigid outer socket having an internal locking groove located at some point between the distal and proximal ends thereof. The locking groove is adapted to receive and releasably interlock with a seal element of like shape that extends circumferentially around and protrudes from the sealing sleeve at a distal end thereof.

The proximal end of the sealing sleeve extends beyond the open proximal end of both the soft inner socket and rigid outer socket to contact and seal against a portion of the prosthetic liner that also extends beyond the open end of the soft inner socket and rigid outer socket. As with previous embodiments, the proximal open end of the prosthetic liner may be reflected or the liner may be provided with an area of exposed polymeric material against which the sealing sleeve may seal.

In a variation of this embodiment, the present invention generally includes a prosthetic liner, such as a polymeric prosthetic liner with a fabric—covered exterior, for donning over an amputee's residual limb; a soft inner socket for receiving a portion of the liner-covered residual limb; and an open-ended polymeric sealing sleeve (which may have a partially fabric-covered exterior) having a distal portion that overlies the soft inner socket. This embodiment also includes a rigid outer socket having an internal locking groove locate at some point between the distal and proximal ends thereof.

The locking groove of this embodiment is preferably hook-shaped or half arrowhead-shaped at its proximal terminus, and is designed to mate with a correspondingly-shaped sealing element that extends Circumferentially around and protrudes from the sealing sleeve at a distal end thereof. The shape of the cavity is able to account for a slight distal or proximal misalignment of the sealing element after initial donning, while also ensuring that the sealing element is forced into proper alignment with the locking groove once vacuum is applied.

The proximal end of the sealing sleeve again extends beyond the proximal open end of both the soft inner socket and rigid outer socket to contact and seal against a portion of the prosthetic liner that also extends beyond the open end of the soft inner socket and rigid outer socket. As with previous embodiments, the proximal open end of the prosthetic liner may be reflected or the liner may be provided with an area of exposed polymeric material against which the sealing sleeve may seal.

Still another exemplary embodiment of a socket sealing system of the present invention generally includes a prosthetic liner for donning over an amputee's residual limb, the liner preferably being a polymeric prosthetic liner with an exterior that is at least partially covered with fabric; a rigid outer socket having an internal and circumferentially-extending seal-receiving groove located near the proximal open end thereof and preferably substantially tracing the shape of the socket brim; and a seal element adapted for location within the seal-receiving groove and to protrude by some amount therefrom so as to seal against the prosthetic liner when the liner is worn by an amputee and the socket is donned.

In this embodiment, the seal element is preferably rod or rope-shaped, as is the corresponding seal-receiving groove. The seal element is preferably comprised of a polymeric material such as silicone, and may have a central (axially-oriented) wire running through all or a portion of its length. The wire allows the seal element to retain bends that are imparted thereto, such as the bends that may be required to follow the shape of a prosthetic socket brim.

The prosthetic socket is sealed for vacuum suspension by contact of the seal element with the exterior of the prosthetic liner. To this end, the fabric covering on the exterior of the liner either terminates at a point that is located distally of the seal element, or an area of the fabric covering may be removed along the area of the seal element, such that the seal element is in contact with the polymeric material of the prosthetic liner.

As should be understood from the exemplary embodiments described above, socket sealing systems of the present invention are effective for use either with (passive) suction or (active) elevated vacuum suspension. In the former case, all sealing system embodiments according to the invention may be used with a one-way valve, which allows air to be forced out of the socket but does not allow air to enter. In the latter case, all sealing system embodiments according to the invention may be used with an evacuation system, which may include a battery-powered vacuum pump. In this regard, the rigid outer sockets of embodiments of the invention may be equipped with internal adapters that function, without limitation, to receive the distal end of a liner-covered (and possibly soft socket-covered) residual limb, to provide a vacuum path between the atmosphere and the socket interior, and to couple an evacuation device to the socket. When a soft inner socket is used, the distal end of the soft socket may be modified to have an opening via which vacuum can be applied to the liner-covered residual limb. When a sealing sleeve having a closed end is placed over a soft inner socket, it may be similarly modified.

At least certain socket sealing systems of the present invention have the ability to follow the contours of a socket brim or any other contour desired so as to maximize the surface area for suspension. In other embodiments, the wicking nature of the fabric covering on the exterior of the prosthetic liner allows evacuation of air from across substantially the entire outer surface of that portion of the liner that resides within socket(s). Consequently, socket sealing systems of the present invention allow the vacuum to be spread over a larger surface area than is possible with known systems, which results in better suspension and potential health benefits for the tissue underlying the evacuated area.

Socket sealing systems of the present invention also allow for the use of non-cylindrically shaped sockets, which permit an optimized fit to the residual limb and prevent rotation. This is in contrast to known systems that require a substantially cylindrical shape in order for the seal to function properly, which results in limited resistance to rotation of the socket about the limb. Socket sealing systems of the present invention also permit the use of sockets with lower trim lines, which enhances range of motion, comfort, and liner life.

A better understanding of socket sealing systems of the present invention can be gained by review of the following description of several exemplary embodiments thereof, along with the associated accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 2 is an enlarged front sectional view of the components of FIG. 1 in an assembled condition;

FIG. 3 is an enlarged detail view of the area indicated on FIG. 2;

FIG. 4 is an isometric sectional view of a liner and sealing ring element of another exemplary embodiment of a socket sealing system of the present invention;

FIG. 5 is an enlarged front sectional view of the components of FIG. 4;

FIG. 8A is a cross-sectional view of another exemplary embodiment of a socket seating system of the present invention, wherein a soft inner socket is present;

FIG. 8B shows the socket sealing system of FIG. 8A with the prosthetic liner thereof in a non-reflected orientation;

FIG. 11A is a cross-sectional view of another exemplary embodiment of a socket sealing system of the present invention that is similar to the embodiment of FIG. 10A but also includes a soft inner socket;

FIG. 11B shows the socket sealing system of FIG. 11A with the prosthetic liner thereof in a non-reflected orientation;

FIGS. 14A and 14B illustrate another exemplary embodiment of a socket sealing system of the present invention, wherein a groove in a rigid socket engages a sealing element of a sealing sleeve;

FIGS. 16A-16C depict a sealing sleeve with exemplary alternative sealing elements;

FIG. 19 illustrates optional socket evacuation-related components that may be used with a socket sealing system of the present invention.

DETAILED DESCRIPTION OF THE EXEMPLARY EMBODIMENT(S)

Figure 1:
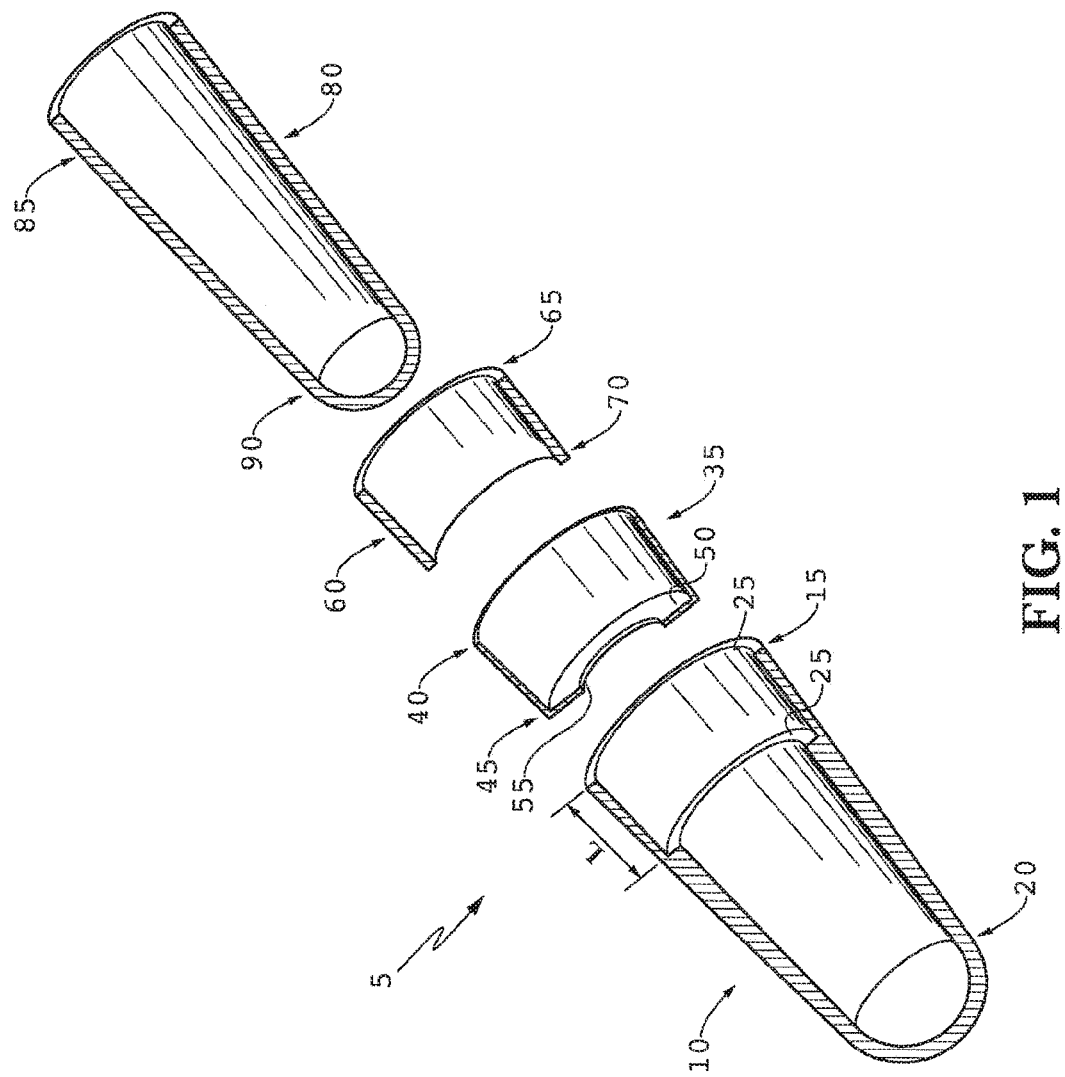
FIG. 1 is an exploded isometric sectional view of one exemplary embodiment of a socket sealing system of the present invention.
Figure 7:
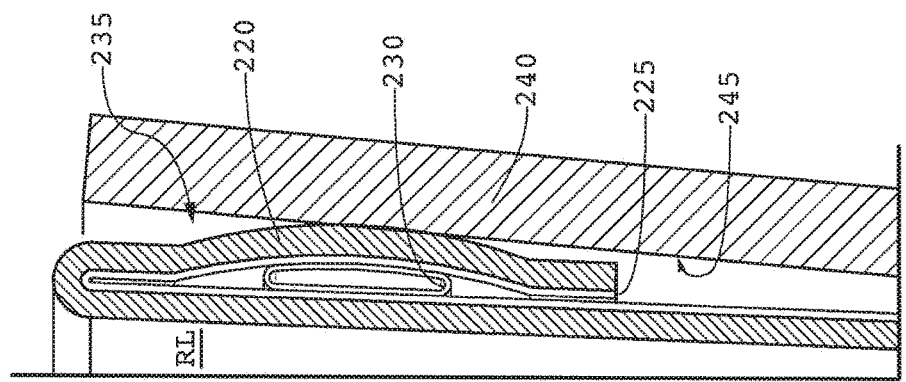
FIG. 7 is an enlarged detail view of the area indicated on FIG. 6.
Figure 6:
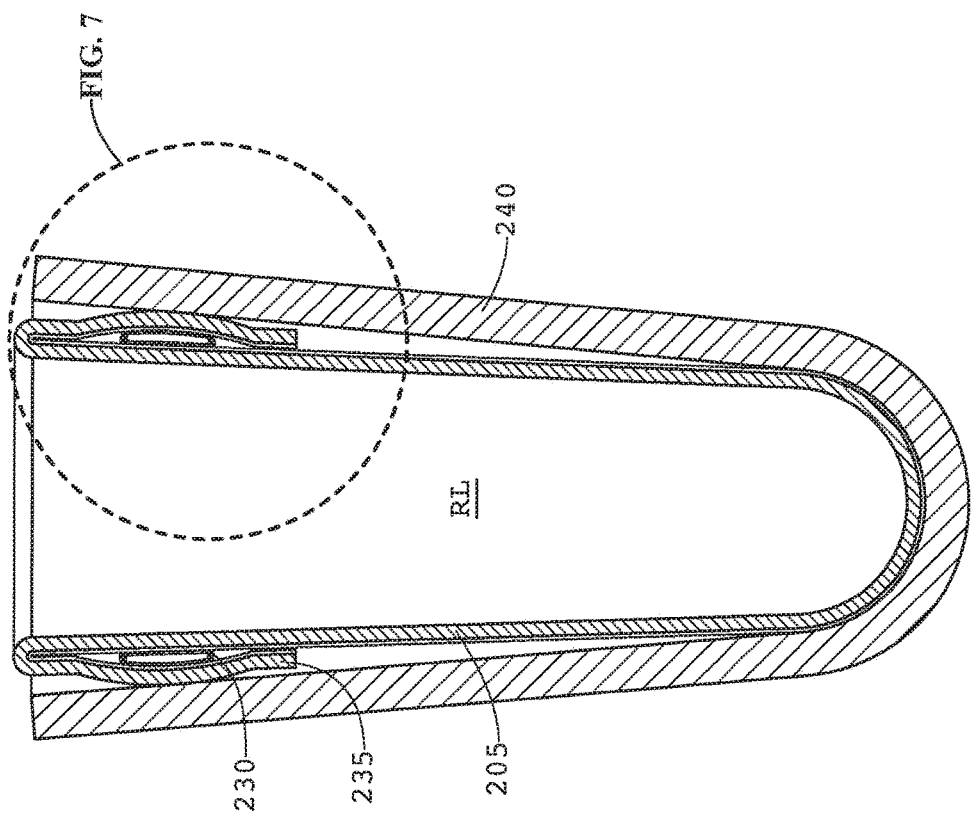
FIG. 6 depicts the components of FIGS. 4-5 installed to a residual limb and inserted into a prosthetic socket.

Exemplary embodiments of a socket sealing system of the present invention are described below. These exemplary embodiments are provided solely for the purpose of illustration, and not limitation. It should be noted that the dimensions of the various system components may be exaggerated in the drawing figures for the purpose of clarity. The exemplary embodiments described below and shown in the drawing figures may be particularly well-suited for use in a TF prosthesis, but may also be used with a TT prosthesis or an upper extremity prosthesis.

A first exemplary embodiment of a socket sealing system (hereinafter "system") 5 of the present invention is depicted in FIGS. 1-3. As shown, the system 5 includes a prosthetic socket 10 having an open end 15 for permitting insertion of a residual limb RL, and a closed end 20 opposite the open end. The sealing system 5 also includes a sealing membrane 35 and an inner brim component 60. A prosthetic liner 80 may optionally be used with the sealing system 5.

The socket 10 may be much like a typical prosthetic socket, except that a section 25 of the interior periphery at the proximal end 15 is of greater dimension than the interior periphery at a more distal location. More specifically, an area 25 of the interior periphery of the socket 10 that extends from the proximal end 15 some length L toward the distal end 20 is deliberately enlarged beyond what is necessary to receive a residual limb RL in order to produce additional interior socket space for receiving the inner brim 60 and a portion of the sealing membrane 35. This results in a peripheral shoulder 30 within the socket 10, and typically a thinner socket wall within the area 25 of increased inner peripheral dimension (although the socket could be modified (e.g., stepped outward) to maintain substantially the same socket wall thickness).

The sealing membrane 35 is preferably a thin-walled band or tube of flexible elastomeric material. As shown, the sealing membrane 35 is of some length that will generally depend at least somewhat on the length L of the enlarged interior periphery area 25 of the socket 10, and includes a proximal end 40 and a distal end 45. The overall shape of the sealing membrane 35 may be substantially tubular, or may be frustoconical wherein the membrane tapers inward from the proximal end toward the distal end. Custom membrane shapes are also possible.

The dimension of the interior periphery at the proximal end 40 of the sealing membrane 35 is selected to permit the proximal portion of the sealing membrane to be pulled (stretched) over a distal exterior portion of the inner brim 60 (see FIGS. 2-3), although the membrane may also be designed to cover the exterior of the inner brim to a greater extent. The distal end 45 of the sealing membrane 35 may include a sealing section 50 having a central opening 55 of reduced size in comparison to the opening at the proximal end 40 of the sealing membrane. The reduced size of the distal opening 55 may result from a tapering membrane shape or simply from the fact that the proximal end 40 of the membrane 35 has been stretched to fit over the inner brim 60.

As described in more detail below, the sealing section 50 of the sealing membrane 35 seals against the skin of a residual limb RL or the exterior of a prosthetic liner when in use. Consequently, it should be apparent that the exact dimension and shape of the distal opening 55 may be adjusted to best accommodate a given residual limb RL. Alternatively, it is also possible to supply sealing membranes with a distal opening of one standard shape and dimension, or with a small number of different shapes and/or dimensions, which distal opening(s) will effectively allow the sealing membranes to seal against the vast majority of bare or liner-covered residual limbs without causing amputee discomfort, acting as a tourniquet, etc.

The sealing membrane 35 may be constructed from various elastomeric materials including, but not limited to, silicone, rubber, urethane, and latex. The sealing membrane 35 may optionally include a reinforcing material, especially a one-way stretch reinforcing material that prevents an over-stretching of the sealing membrane into the socket 10 during residual limb insertion. Such a reinforcing material may also provide for improved shape conformance and durability.

The inner brim 60 is also preferably provided in the form of a ring or tube, which may have a regular or irregular peripheral shape. The shape of the inner brim 60 may also be substantially frustoconical-tapering inward from a proximal end 65 toward a distal end 70. The shape of the inner brim 60 may also be customized to intimately interface with a customized interior wall of a given prosthetic socket and to the shape of the wearer's limb.

The inner brim 60 may be comprised of a substantially rigid material. Alternatively, the inner brim 60 may be constructed from a somewhat flexible material such as polyethylene or an ethylene-vinyl acetate (EVA) material such as, for example, ThermoLyn® from Otto Bock® or Northvane™ from North Sea Plastics, in Glasgow, Scotland.

The thickness and length of the inner brim 60 may also vary. The thickness of the inner brim 60 will be largely dependent on the interior peripheral dimension of the receiving section 25 of the prosthetic socket 10 and the thickness of the proximal portion 40 of the sealing membrane 35 that fits over the inner brim. The length of the inner brim 60 may be dependent on the length L of the area 25 of enlarged interior socket periphery, the length of a liner used with the system 5, the length of an amputee's residual limb above the socket brim when wearing the associated prosthesis, etc. In any event, the thickness and/or length of the inner brim 60 may be adjusted as needed.

The sealing system 5 may be worn by an amputee without a liner or other prosthetic limb covering. In this case, the skin of the residual limb RL is in direct contact with the interior of the prosthetic socket and the sealing membrane 35 seals against the skin of the residual limb. Alternatively, a limb covering such as a prosthetic liner 80 may be used with the socket sealing system 5. As shown, such a prosthetic liner 80 has an open end 85 for permitting insertion of a residual limb, and a closed end 90 opposite the open end. When a liner 80 is used, the interior of the liner resides against the skin of the residual limb RL and the exterior of the liner resides against the interior of the prosthetic socket 10. As is described in more detail below, the sealing membrane 35 also seals against the exterior of the liner 80 in this case and a portion of the liner exterior also abuts the interior wan of the inner brim 60.

When a liner 80 is used, the liner may be of various design/construction. For example, and as is illustrated in FIGS. 1-3, the liner may have a polymeric material 95 interior and an integral fabric exterior 100. The polymeric material of the liner interior will be in contact with the skin of a residual limb when the liner is worn, while the fabric exterior of the liner will be in contact with the interior of the prosthetic socket 10. The aforementioned Alpha® Liner series of prosthetic liners from The Ohio Willow Wood Company have such a construction. Liners of other construction may also be employed, such as liners without a fabric exterior or liners partially covered with fabric. The polymeric material of a liner of the present invention may be a silicone, urethane, thermoplastic elastomer or other polymeric material from which it is known or possible to make a prosthetic liner. In any case, the sealing membrane 35 must be able to seal against the exterior of the liner.

FIGS. 2-3 illustrate how the components shown in FIG. 1 are assembled and interrelate after a liner-covered residual limb RL has been properly inserted into the socket. As shown, the proximal portion 40 of the sealing membrane 35 is pulled over the exterior of the inner brim 60. The inner brim/sealing membrane assembly is then inserted into the prosthetic socket 10 until a portion of the sealing membrane resides against the shoulder 30 in the socket. The inner brim 60 preferably fits tightly within the socket 10 such that the inner brim traps the sealing membrane 35 tightly against the shoulder 30 in the socket—thereby securing (and possibly sealing) the membrane to the socket. The inner brim 60 also traps and seals the overlying proximal portion of the sealing membrane 35 against the interior wall of the socket 10. In this regard, the sealing membrane may also have a series of vanes or ribs along the proximal exterior surface thereof that may be compressed between the interior surface of the prosthetic socket and the exterior surface of the inner brim. The vanes/ribs may act as gap fillers that enhance the seal between the membrane and the socket interior. Vanes/ribs may also be located along the proximal interior surface of the membrane for seal enhancing reasons.

With the inner brim/sealing membrane assembly installed in the socket 10 as described above, an amputee's residual limb RL may be inserted into the socket. As shown in FIGS. 2-3, a prosthetic liner 80 is donned over the residual limb RL before the residual limb is inserted into the socket 10 in this embodiment. In other embodiments, a bare residual limb may be inserted into the socket or a different limb covering may be donned over the residual limb. Thus, in other embodiments, the skin of the residual limb or an exterior surface of another limb covering will function as is described below with respect to the exterior of the liner 80.

As the liner-covered residual limb RL is inserted into the socket 10, the limb passes through the opening 55 in the distal portion 45 of the sealing membrane 35. Because the opening 55 is of a peripheral dimension that is smaller than the exterior peripheral dimension of the liner-covered residual limb AL, the elastomeric material in the area of the opening is stretched and remains in sealing contact with the exterior of the liner 80. The distal portion of the sealing membrane is preferably of sufficient length to extend distally into the socket for some distance past the shoulder 30 after the residual limb RL has been inserted, which enhances the sealing contact between the membrane and the liner (or limb). The interior of the socket 10 is thus sealed against air leaks through its proximal end and may be evacuated.

It is preferable that a liner used with the socket sealing system 5 has an exterior surface that allows vacuum forces to be distributed over as much of the liner exterior residing below the seal as possible. This helps to ensure greater suspension and the distribution of vacuum benefits over as much of the residual limb as possible. This distribution of vacuum forces may be enhanced by covering the liner with fabric (as described) or another wicking material. Alternatively, or in conjunction therewith, grooves may be molding into the outside surface of a liner.

While it may be possible to create a seal between a sealing membrane and the fabric exterior of a prosthetic liner (depending on the fabric), such a seal may be enhanced by providing a fabric-free section (e.g., band) about the exterior of the liner in the area that will contact the sealing membrane. Such a construction may be achieved, for example, by constructing a liner without fabric in the applicable area (so that the underlying polymeric material is exposed) or by applying a band of elastomeric material over the exterior fabric of the liner in the applicable area. Alternatively, a liner without a fabric covering may be used, such that the entire liner exterior is comprised of polymeric material.

In a variation (not shown) of this exemplary embodiment, it may be possible to eliminate the modifications to the prosthetic socket—including the shoulder and enlarged proximal interior portion—by placing a rib(s) on the exterior of the inner brim and a corresponding receiving groove(s) in the interior of the socket. In this case, the proximal portion of the sealing membrane is stretched over the rib(s) when the sealing membrane is installed to the inner brim. Upon installation of the sealing membrane/inner brim assembly into the prosthetic socket, the membrane-covered rib(s) is engaged in the receiving groove(s) of the socket, thereby securing and sealing the membrane to the socket interior.

An alternative exemplary embodiment of a sealing system 200 of the present invention is illustrated in FIGS. 4-7. This embodiment of the present invention generally includes a prosthetic liner 205 for donning over an amputee's residual limb RL, and an elastomeric sealing ring 230 for sealing a portion of the prosthetic liner against an interior wall 245 of a prosthetic socket 240. This embodiment of the socket sealing system 200 may be used with substantially any standard prosthetic socket, such as the prosthetic socket of an existing prosthesis. Note that the residual limb RL is not shown to extend beyond the socket in FIGS. 4-7 only for purposes of clarity.

The liner 205 used with this embodiment of the socket sealing system 200 may again be of various design/construction. As shown, the liner includes an open end 210 for permitting insertion of a residual limb RL, and a closed end 215 opposite the open end. The liner 205 may again have a polymeric material 220 interior and an integral fabric exterior 225, such as an Alpha® Liner from The Ohio Willow Wood Company. With this construction, the polymeric material 220 of the liner interior will be in contact with the skin of the residual limb RL when the liner is worn, while the fabric exterior 225 of the liner will be in contact with the interior of the prosthetic socket 240. Liners of other construction may also be employed, such as liners without a fabric exterior. The polymeric material of a liner of the present invention may be a silicone, urethane, thermoplastic elastomer or other polymeric material from which it is known or possible to make a prosthetic liner. However, in any case the liner must be capable of seating against the interior wall of a socket and of being reflected at its proximal end, as is described in more detail below.

The inflatable elastomeric sealing ring 230 is generally thin-walled and may be substantially round or oval in cross-section (although other cross-sectional shapes are also possible). The sealing ring 230 is thus in the general shape of an inner-tube or donut with a central opening passing there through as normal. The enclosed interior volume of the sealing ring 230 contains some amount of air or another gas at some pressure.

Preferably, the circumferential dimension of the central opening of the sealing ring 230 when inflated is less than the external peripheral dimension of the liner-covered residual limb over which the sealing ring will be installed, such that the sealing ring will fit sufficiently snugly around the liner-covered limb and tend to remain where placed by the amputee. The sealing ring 230 can be made of a variety of elastomeric materials including, for example, silicone, rubber, urethane, and latex.

To use this embodiment of the sealing system 200, an amputee first dons the prosthetic liner 205, then slides the sealing ring 230 over the exterior of the liner to a point near the proximal end 230 thereof. The proximal end 210 of the liner 205 is then reflected over the sealing ring 230 as shown, such that the sealing ring is sandwiched between a reflected portion 235 of the liner and a portion of the liner that resides against the residual limb. The reflected proximal edge of the liner may be secured to the non-reflected portion of the liner at the point of contact there between. This may be accomplished by a number of techniques, including releasable adhesives or other non-permanent fastening means. In an alternative embodiment (not shown), the reflected proximal edge of the liner may be permanently secured to the non-reflected portion of the liner such that the sealing ring is permanently trapped there between.

The liner-covered residual limb with the sealing ring 230 is then inserted into the prosthetic socket 240 so that the sealing ring and at least some of the reflected portion 235 resides within the socket. As can be best observed in FIG. 7, the polymeric material 220 of the liner 205 faces outward on the reflected portion 235 of the liner. Thus, the polymeric material 220 of the reflected portion 235 of the liner 205 is in contact with the interior wall 245 of the socket 205 in the area of the sealing ring 230.

With the liner-covered residual limb RL and the sealing ring 230 inserted into the socket 240 as shown, air may be evacuated from the socket interior. As the interior of the socket 240 is evacuated, the sealing ring 230 will expand, pressing the reflected portion 235 of the liner 280 against interior wall 245 of the socket. It is believed that this expansion of the sealing ring 230 is due to a pressure differential that develops between the gas trapped within the sealing ring and the atmosphere within the socket as the socket interior is evacuated. In any event, expansion of the sealing ring 230 results in a seal between the polymeric material 220 of the reflected portion 235 of the liner 205 and the interior wall 245 of the socket 240, which seals the socket interior against the entrance or exit of air through the proximal (open) end 210 of the socket. Consequently, the socket interior may be evacuated for the purpose of vacuum suspension of a prosthesis or for other purposes, and an acceptable level of vacuum may be maintained during wearing of the prosthesis.

It has been found that a socket sealing system employing an inflatable sealing ring better maintains a seal of the socket interior because the gas trapped in the sealing ring is pushed from areas of high pressure to areas of low pressure, which thereby helps to maintain a seal against the socket wall in areas where the residual limb would normally pull away from the socket. For example when a TF amputee is sitting down, the pressure along the posterior portion of the socket is high and pushes fluid into a low pressure area along the anterior portion of the socket, thereby filling any voids and maintaining the seal.

Variations of this sealing ring embodiment are also possible. For example, an inflatable sealing ring could be incorporated into or onto a liner, thereby eliminating the need for the liner to be reflected over the sealing ring at the proximal end. In this case, the sealing ring could be bonded to the liner with an adhesive or an elastomeric material. It may also be possible to integrate the seating ring into the liner by some molding process. In this variation, the inflatable sealing ring is preferably comprised of a material that will seal well against the interior wall of a socket, or is at least provided with a peripheral section of such a material along the line of socket contact.

In another variation, it may be possible to attach an inflatable sealing ring to the interior wall of a socket, such that a permanent seal is created between the sealing ring and the socket wall. This would also eliminate the need for the liner to be reflected over the sealing ring at the proximal end. In this variation, the inflatable sealing ring would be adapted to seal against the skin of a residual limb or the exterior of a liner. In the latter case, the liner may also be adapted to facilitate a seal with the sealing ring. When the liner has a fabric exterior, this may be accomplished, for example, by removing a section of fabric to expose a band of underlying polymeric material or by applying a band of polymeric material to the exterior of the fabric. In this variation, it may also be possible to pass a valve stem or similar element from the inflatable sealing ring through the socket wall, such that the volume of air or other gas in the sealing ring may be adjusted from outside the socket.

Yet another variation of the present invention may combine elements of the first and second exemplary embodiments described above. More particularly, an inflatable sealing ring may be attached to an inner brim element and located in a prosthetic socket upon insertion of the inner brim. In this variation, the inflatable sealing ring would again be adapted to seal against the skin of a residual limb or the exterior of a liner in any manner previously described or otherwise known in the art.

Another exemplary embodiment of a socket sealing system (hereinafter "system") 300 of the present invention is depicted in FIG. 8A. As shown, the system 300 includes a rigid outer prosthetic socket 305; a polymeric prosthetic liner 310 for donning over an amputee's residual limb, the liner having a polymeric material interior 315 and an exterior fabric covering 320; a soft inner socket 325 for receiving a portion of the liner-covered residual limb; and a polymeric sealing sleeve 330, the exterior of which may be partially or wholly covered with fabric (not shown). The sealing sleeve 330 is pulled over and seals against the soft inner socket 325. Each of the outer prosthetic socket 305, prosthetic liner 310, soft inner socket 325 and sealing sleeve 330 has an open proximal end for permitting insertion of a residual limb, and a closed distal end opposite the open end.

The combination of the prosthetic liner 310, soft inner socket 325 and sealing sleeve 330 are placed on a residual limb and the residual limb is thereafter inserted into the rigid prosthetic socket 305. A proximal portion of the prosthetic liner 310 extends beyond the open ends of the soft and rigid sockets 315, 305. In this embodiment, the proximal open end 310a of the prosthetic liner 310 is reflected such that the polymeric material 315 thereof is exposed. A proximal portion of the sealing sleeve also extends beyond the open ends of the soft and rigid sockets 325, 305. Sealing of the liner 310 to the sleeve 330 is accomplished by overlapping the reflected proximal end 310a of the liner 310 with the proximal open end 330a of the polymeric sealing sleeve. When a vacuum is subsequently drawn, the sealing sleeve 330 will be tightly drawn against the exterior of the liner 310 in the area between the proximal end of the sockets 305, 325 and the reflected proximal end 310a of the liner.

A variation of the embodiment of FIG. 8A is shown in FIG. 8B. In this embodiment, the fabric covering 320 on the exterior of the prosthetic liner 310 terminates prior to reaching the proximal open end 310a of the liner. In this case, the proximal end 310a of the liner 310 is not reflected as in the embodiment of FIG. 8A. Rather, the polymeric material of the sealing sleeve 330 contacts and seals against the exposed polymeric material 315 of the liner 310.

In an alternative embodiment (not shown), only a section of the liner fabric covering 320 may be removed, thus leaving a circumferential band of exposed polymeric material 315 along a portion of the liner 310 that extends beyond the soft and rigid sockets 305, 325. In this case, the polymeric material of the sealing sleeve 330 again contacts and seals against the exposed polymeric material 315 of the liner 310, but a more proximal portion of the liner may still have a fabric exterior to help prevent the sticking thereto of an amputee's clothing, etc.

Figure 8C:
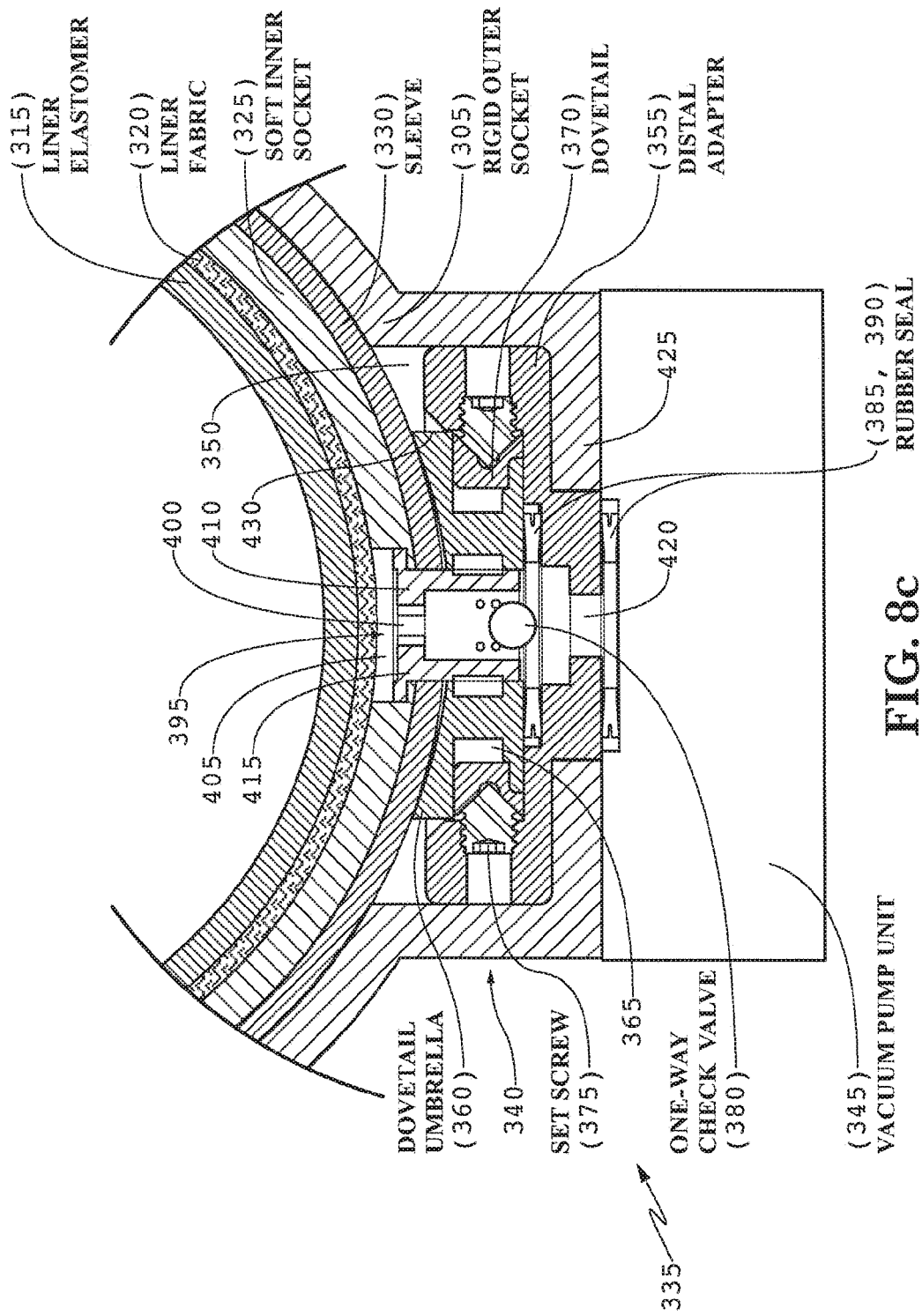
FIG. 8C is a cross-sectional view showing various details of an exemplary vacuum assembly that may be used with the exemplary embodiments of FIGS. 8A-8B, and possibly with other embodiments of the invention.

An enlarged detail view of the exemplary vacuum suspension assembly 335 shown in FIGS. 8A-8B is shown in FIG. 8C. As can be observed, the vacuum suspension assembly 335 includes a socket-located portion 340 and an external vacuum unit 345 that is attached to the distal end of the rigid prosthetic socket 305 and coupled to the socket-located portion 340 of the vacuum suspension assembly.

The socket-located portion 340 includes an adapter 355 that is located in a cavity 350 at the distal end of the rigid prosthetic socket 305. The adapter 355 may be substantially disk-shaped, but the exact configuration may vary. The adapter 355 is designed to engage a substantially umbrella-shaped dovetail element 360 (e.g., dovetail umbrella) that is molded to, bonded to, or otherwise attached to the sealing sleeve 330 at the exterior distal end thereof. The dovetail umbrella 360 may be comprised of, for example, a material such as urethane.

A one-way check valve 380 may be provided to ensure that air evacuated by the vacuum unit 345 cannot return to the socket 325. The check valve 380 is a part of an assembly 395 that includes a hollow T-nut 400, which acts to secure itself and the check valve to the soft inner socket 325 and sealing sleeve 330. In this manner, the soft inner socket 325, the sealing sleeve 330 and the check valve 380, as well as the dovetail umbrella (360) are donnable and doffable as a single unit. The liner contacting portion 405 of the T-nut may be shaped and comprised of a material that facilitates its conformity to the shape of the liner 310. Both the soft inner socket 325 and the sealing sleeve 330 are provided with apertures 410, 415 that permit passage of the T-nut 400 and check valve 380.

The adapter 355 includes a dovetail umbrella receiving cavity 430 and may be releasably coupled to the dovetail umbrella 360 by engaging slots 365 in the umbrella with dovetail elements 370 of the adapter. The dovetail elements 370 may be engaged with the slots 365 by means of, for example, corresponding set screws 375. Set screw access holes (not shown) are provided in the socket walls to permit access to the set screws after the liner/soft socket/sleeve-covered residual limb is inserted therein.

Rubber or similar seals (e.g., O-rings) 385, 390 may be provided to seal the pathway 420 through the adapter 355 that connects the vacuum unit 345 to the check valve 380.

To assemble this system, the adapter 355 is first secured within the cavity 350 in the rigid prosthetic socket 305. The assembly of the soft inner socket 325, sealing sleeve 330, and accompanying dovetail umbrella 360 and check valve 380 are then inserted into the prosthetic socket 305 until the dovetail umbrella 360 is seated in the adapter 355 and the check valve 380 engages the rubber seal 385 located in the adapter. Installation of this assembly may be facilitated by first placing it over an amputee's residual limb and having the amputee step into the prosthetic socket 305. With the dovetail umbrella 360 and check valve 380 properly seated, the set screws 375 may be tightened via the provided set screw access holes, thereby locking the soft inner socket 325, sealing sleeve 330, dovetail umbrella 360 and check valve 380 assembly to the adapter 355, and to the prosthetic socket.

To use this system, an amputee dons the prosthetic liner 310, and inserts the liner-covered residual limb into the soft inner socket 325 that is now located within the rigid prosthetic socket 305. Subsequent operation of the vacuum unit 345 then evacuates air trapped between the prosthetic liner 310 and the interior of the soft inner socket 325, which is sealed to the prosthetic liner by the sealing sleeve 330 as described above. The sealing sleeve 330 may also seal against the interior of the rigid prosthetic socket 305. Consequently, as air is evacuated by the vacuum unit 345, the liner-covered residual limb is drawn securely against the soft inner socket 325. Because of the wicking ability of the fabric exterior 320 of the prosthetic liner 310, the drawing force exerted by the vacuum is spread over substantially the entire exterior surface of that portion of the liner residing in the prosthetic socket 305. A highly secure suspension of the associated prosthesis on the residual limb is thus achieved. When an amputee is ready to remove the prosthesis, the vacuum may be released by simply breaking the seal between the prosthetic liner 310 and the sealing sleeve 330.

The vacuum unit 345 may be attached to the prosthetic socket 305 before or after an amputee inserts the residual limb into the prosthetic socket. The vacuum unit 345 may be attached directly to the prosthetic socket 305 if the socket is appropriately adapted (e.g., by means of threaded inserts, etc.). Alternatively, the vacuum unit 345 may be attached by securing the vacuum unit to the adapter 355 using threaded fasteners that are passed through holes (not shown) in the prosthetic socket 305 so as to trap the distal wall 425 of the adapter cavity 350 therebetween.

Figure 9:
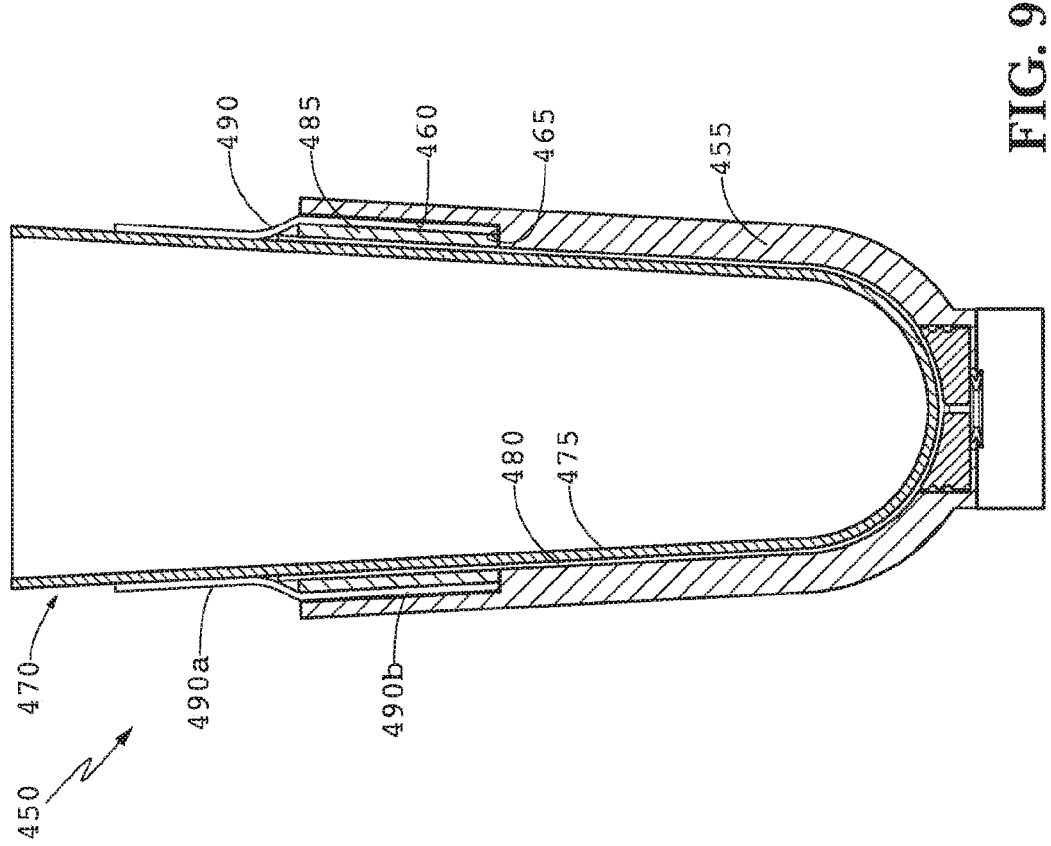
FIG. 9 is a cross-sectional view of another exemplary embodiment of a socket sealing system of the present invention where an inner brim component is present.

Another exemplary embodiment of a socket sealing system (hereinafter "system") 450 of the present invention is depicted in FIG. 9. As shown, the system 450 includes a rigid outer prosthetic socket 455 having an open proximal end, a closed distal end, and an area of relief 460 along the interior of its proximal end that results in a peripheral shoulder 465 within the socket. A polymeric prosthetic liner 470 for donning over an amputee's residual limb is also included, the liner having a polymeric material interior 475 and an exterior fabric covering 480. Like the prosthetic socket 455, the prosthetic liner 470 also has an open proximal end for permitting insertion of a residual limb, and a closed distal end opposite the open end.

In this embodiment, the soft inner socket of the embodiment shown in FIGS. 8A-8B is replaced with a ring-like soft inner brim component 485 of regular or irregular peripheral shape that is designed to entirely within the relief area 460 of the rigid prosthetic socket 455 and have a thickness less than the depth of the relief or receiving section of the socket. An open-ended polymeric sealing sleeve 490 is also provided, and may have a partially fabric-covered exterior. A distal portion 490b of the polymeric sealing sleeve 490 is arranged to reside within the relief area 460 of the rigid prosthetic socket 455, and between the prosthetic socket and the brim component 485. The distal portion 490b of polymeric sealing sleeve 490 thus overlies and seals against the exterior of the brim component 485 and, preferably, also seals against the interior wall of the prosthetic socket 455 in the relief area thereof. A proximal portion 490a of the polymeric sealing sleeve 490 is designed to extend from the rigid prosthetic socket 455 and to seal against a portion of the prosthetic liner (or residual limb) that also extends from the rigid prosthetic socket.

As shown, the fabric covering 480 on the exterior of the prosthetic liner 470 may again terminate at some point before reaching the open end thereof, thereby leaving an exposed section of polymeric material 475 near the proximal end of the liner that extends beyond the rigid prosthetic socket 455 and inner brim component 485. In this case, the polymeric material interior of the portion of the sealing sleeve 490 that also extends beyond the rigid prosthetic socket 455 and inner brim component 485 simply contacts and seals against the exposed polymeric material 475 of the liner 470.

In an alternative embodiment (not shown), only a section of the liner fabric covering 480 may be removed, thus leaving a circumferential band of exposed polymeric material 475 along a portion of the liner 470 that extends beyond the rigid prosthetic socket 455 and inner brim component 485. In this case, the polymeric material of the sealing sleeve 490 again contacts and seals against the exposed polymeric material 475 of the liner 470, but a more proximal portion of the liner may still have a fabric exterior to help prevent the sticking thereto of an amputee's clothing, etc.

In another alternative embodiment (not specifically shown), the fabric covering 480 may extend to the proximal end of the liner 470. In this case, the proximal end of the liner 470 may be reflected as shown in FIG. 8A. Sealing of the liner 470 to the sleeve 490 is then accomplished by overlapping the reflected proximal end of the liner 470 with the proximal end of the polymeric sealing sleeve 490.

Figure 10A:
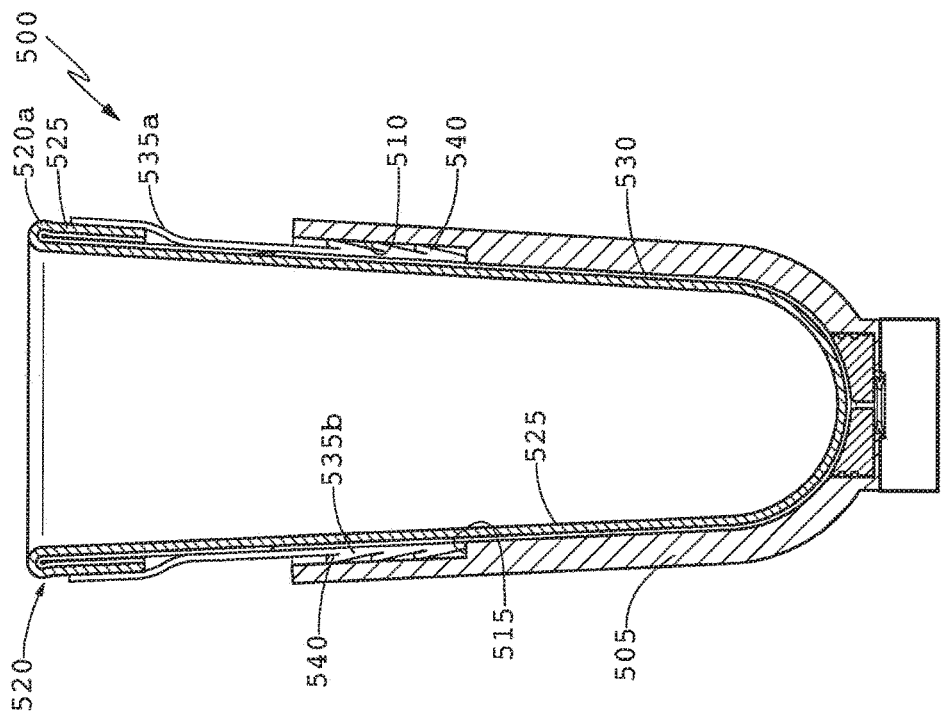
FIG. 10A is a cross-sectional view of another exemplary embodiment of a socket sealing system of the present invention where a sealing sleeve includes sealing elements.

Another exemplary embodiment of a socket sealing system (hereinafter "system") 500 of the present invention is depicted in FIG. 10A. As shown, the system 500 again includes a rigid outer prosthetic socket 505 having an open proximal end, a closed distal end, and an area of relief 510 along the interior of its proximal end that results in a peripheral shoulder 515 within the socket. A polymeric prosthetic liner 520 for donning over an amputee's residual limb is also included, the liner having a polymeric material interior 525 and an exterior fabric covering 530. Like the prosthetic socket 505, the prosthetic liner 520 also has an open proximal end for permitting insertion of a residual limb, and a closed distal end opposite the open end.

An open-ended polymeric sealing sleeve 535 is also provided, and may have a partially fabric-covered exterior. A distal portion 535*b* of the polymeric sealing sleeve 535 is arranged to reside within the relief area 510 of the rigid prosthetic socket 505, between the prosthetic socket and the prosthetic liner 520. The distal portion 535*b* of polymeric sealing sleeve 535 thus overlies the exterior of the prosthetic liner 520, and preferably, also seals against the interior wall of the prosthetic socket 505 in the relief area 510 thereof. A proximal portion 535*a* of the polymeric sealing sleeve 535 is designed to extend from the rigid prosthetic socket 505 and to seal against a portion of the prosthetic liner (or residual limb) that also extends from the rigid prosthetic socket.

In this embodiment, the soft inner brim component 485 of the embodiment shown in FIG. 9 is replaced with one or a plurality of substantially solid sealing elements 540 that are an integral part of and extend from the open-ended sealing sleeve 535 in the area thereof that resides within the relief area of the rigid prosthetic socket 505. The sealing elements 540 may be, for example, one or a plurality of variously shaped protuberances (e.g., vanes) that extend circumferentially around the exterior of the sealing sleeve. The sealing elements 540 are preferably devoid of a fabric covering so as to better seal against the interior of the rigid prosthetic socket 505.

As shown in FIG. 10A, the fabric covering 530 on the exterior of the prosthetic liner 520 may again terminate at some point before reaching the open end thereof, thereby leaving an exposed section of polymeric material 525 near the proximal end of the liner that extends beyond the rigid prosthetic socket 505. In this case, the polymeric material interior of the portion of the sealing sleeve 535 that also extends beyond the rigid prosthetic socket 505 simply contacts and seals against the exposed polymeric material 525 of the liner 520.

Figure 10B:
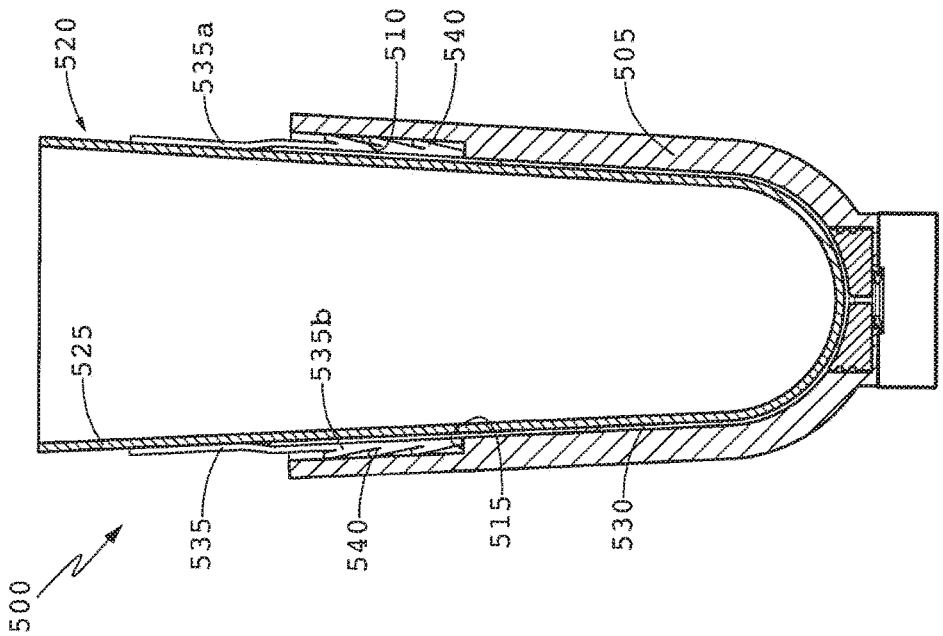
FIG. 10B shows the socket sealing system of FIG. 10A with the prosthetic liner thereof in a reflected orientation.

In the alternate embodiment of FIG. 10B, the fabric covering 530 of the prosthetic liner 520 extends to the proximal end thereof. In this case, the proximal end 520*a* of the liner 520 may be reflected as shown, such that the polymeric material 525 thereof is exposed. Sealing of the liner 520 to the sleeve 535 is then accomplished by overlapping the reflected proximal end 520*a* of the liner 520 with the proximal end 535*a* of the polymeric sealing sleeve 535.

Another exemplary embodiment of a socket sealing system (hereinafter "system") 550 of the present invention is depicted in FIGS. 11A and 11B. As shown, the system 550 includes a rigid outer prosthetic socket 555 having an open proximal end, a closed distal end, and an area of relief 560 along the interior of its proximal end that results in a peripheral shoulder 565 within the socket; a polymeric prosthetic liner 570 for donning over an amputee's residual limb, the liner having a polymeric material interior 575 and an exterior fabric covering 580; a soft inner socket 585 for receiving a portion of the liner-covered residual limb; and a polymeric sealing sleeve 590, the exterior of which may be partially covered with fabric (not shown).

A distal portion 590*b* of the polymeric sealing sleeve 590 is arranged to reside within the relief area 560 of the rigid prosthetic socket 555, between the soft inner socket 585 and the rigid prosthetic socket 555. The distal portion 590*b* of polymeric sealing sleeve 590 thus overlies and seals against the exterior of the soft inner socket 585, and preferably, also seals against the interior wall of the prosthetic socket 555 in the relief area 560 thereof. A proximal portion 590*a* of the polymeric sealing sleeve 590 is designed to extend from the rigid prosthetic socket 555 and soft inner socket 585 and to seal against a portion of the prosthetic liner 570 (or residual limb) that also extends from the rigid prosthetic socket.

In this embodiment, the open-ended sealing sleeve 590 may again include one or a plurality of substantially solid sealing elements 595 that are an integral part of and extend from the sealing sleeve along the area thereof that resides within the relief area 560 of the rigid prosthetic socket 555. The sealing elements 595 may be as described above with respect to the exemplary embodiments of FIGS. 10A-10B. The sealing elements 595 are again preferably devoid of a fabric covering so as to better seal against the interior of the rigid prosthetic socket 555.

As shown in FIG. 11A, the fabric covering 580 of the prosthetic liner 570 extends to the proximal end thereof. In this case, the proximal end 570*a* of the liner 570 may be reflected as shown, such that the polymeric material 575 thereof is exposed. Sealing of the liner 570 to the sleeve 590 is then accomplished by overlapping the reflected proximal end 570*a* of the liner 570 with the proximal end 590*a* of the polymeric sealing sleeve 590.

Alternatively, the fabric covering 580 on the exterior of the prosthetic liner 570 may again terminate at some point before reaching the open end thereof, as shown in FIG. 11B, thereby leaving an exposed section of polymeric material 575 near the proximal end of the liner that extends beyond the rigid prosthetic socket 555 and soft inner socket 585. In this case, the polymeric material interior of the portion of the sealing sleeve 590 that also extends beyond the rigid prosthetic socket 555 and soft inner socket 585 simply contacts and seals against the exposed polymeric material 575 of the liner 570.

Figure 12:
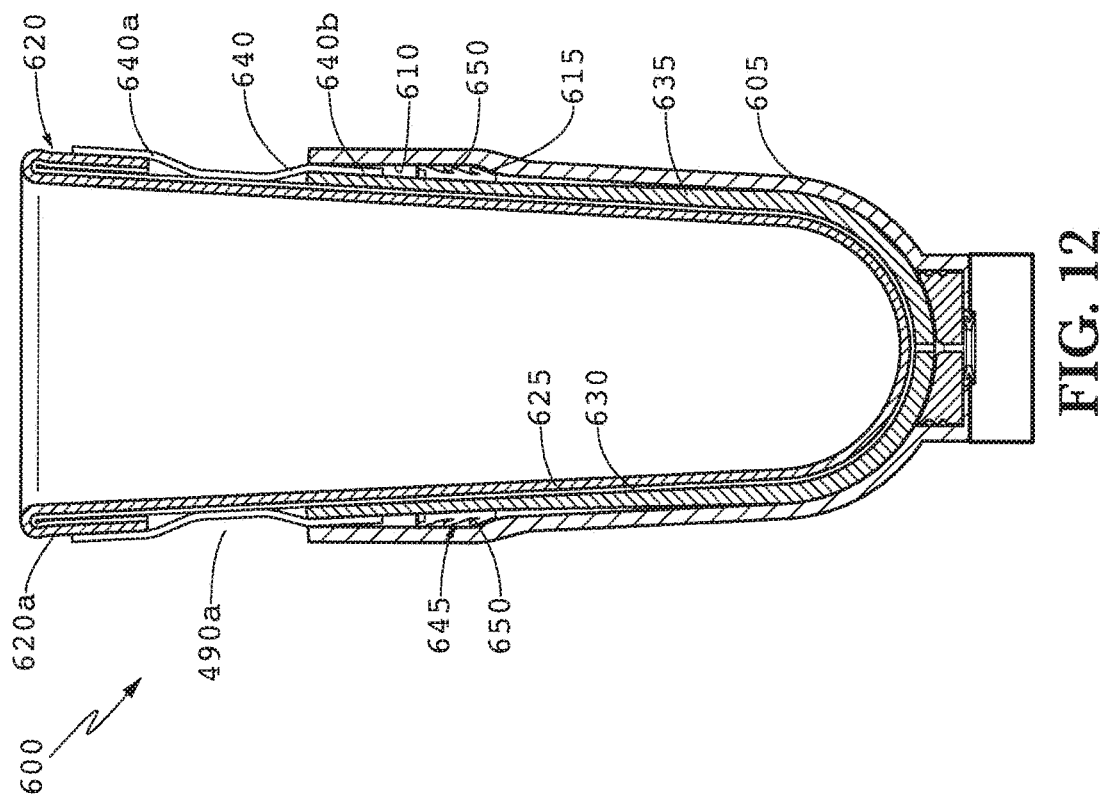
FIG. 12 is a cross-sectional view of another exemplary embodiment of a socket sealing system of the present invention that is similar to the embodiment of FIG. 11A but includes a separate sealing band.

Another exemplary embodiment of a socket sealing system (hereinafter "system") 600 of the present invention is depicted in FIG. 12. As shown, the system 600 includes a rigid outer prosthetic socket 605 having an open proximal end, a closed distal end, and an area of relief 610 along the interior of its proximal end that results in a peripheral shoulder 615 within the socket; a polymeric prosthetic liner 620 for donning over an amputee's residual limb, the liner having a polymeric material interior 625 and an exterior fabric covering 630; a soft inner socket 635 for receiving a portion of the liner-covered residual limb; and a polymeric sealing sleeve 640, the exterior of which may be partially covered with fabric (not shown).

A distal portion 640*b* of the polymeric sealing sleeve 640 is arranged to reside within the relief area 610 of the rigid prosthetic socket 605, between the soft inner socket 635 and the rigid prosthetic socket 605. The distal portion 640*b* of polymeric sealing sleeve 640 thus overlies and seals against the exterior of the soft inner socket 635, and may also seal against the interior wall of the prosthetic socket 605 in the relief area 610 thereof. A proximal portion 640*a* of the polymeric sealing sleeve 640 is designed to extend from the rigid prosthetic socket 605 and soft inner socket 635 and to seal against a portion of the prosthetic liner 620 (or residual limb) that also extends from the rigid prosthetic socket.

In this embodiment, the plurality of sealing elements described as being an integral part of and extending from the open-ended sealing sleeve in the embodiments shown in FIGS. 10A-10B and 11A-11B, are instead part of a separate sealing band 645 that includes the sealing elements 650 and is designed to encircle and seal against the soft inner socket 635 and to reside between the soft inner socket 635 and the rigid outer socket 605 in the relief area 610 thereof. The sealing elements may again be as described above.

The sealing band 645 is employed to provide a seal between the soft inner socket 635 and the rigid outer socket 605, and resides distally of the sealing sleeve 640. The sealing sleeve functions as described above with respect to sealing against the prosthetic liner. In the particular exemplary embodiment shown, the fabric covering 630 of the prosthetic liner 620 extends to the proximal end 640a thereof, and the proximal end is thus reflected as described previously such that the polymeric material 625 thereof is exposed and sealing of the liner 620 to the sleeve 640 is accomplished by overlapping the reflected proximal end 620a of the liner 620 with the proximal end 640a of the polymeric sealing sleeve 640.

Alternatively, the fabric covering 630 on the exterior of the prosthetic liner 620 may again terminate at some point before reaching the open end thereof (not shown), thereby leaving an exposed section of polymeric material 625 near the proximal end of the liner that extends beyond the rigid prosthetic socket 605 and soft inner socket 635. In this case, the polymeric material interior of the portion of the sealing sleeve 640 that also extends beyond the rigid prosthetic socket 605 and soft inner socket 635 simply contacts and seals against the exposed polymeric material 625 of the liner 620.

Figure 13A:
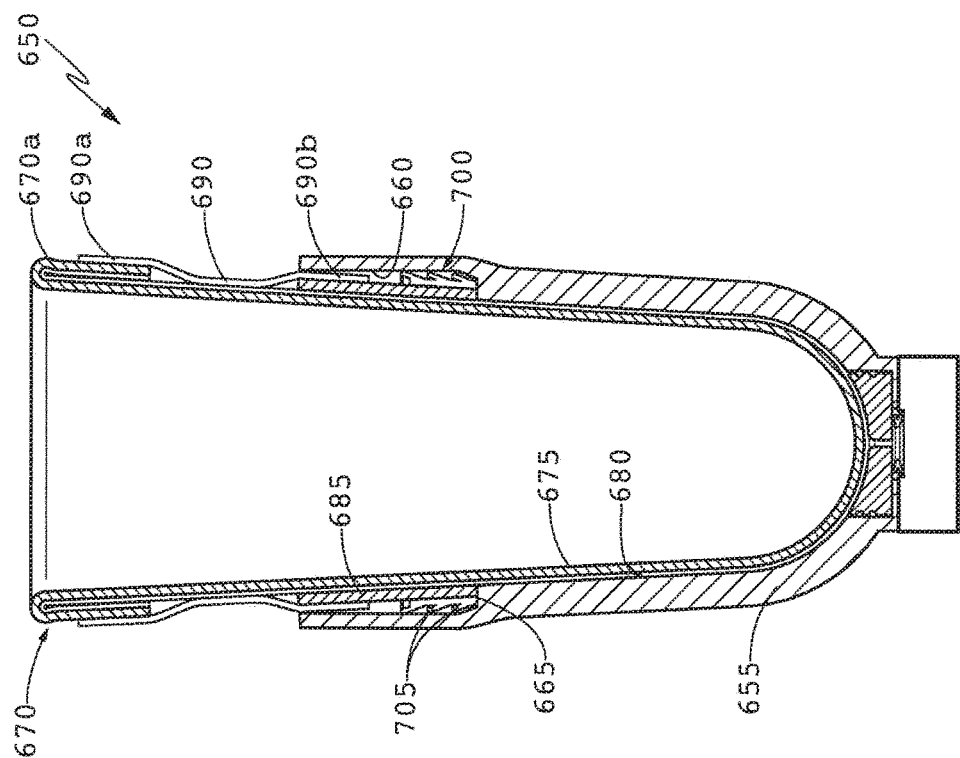
FIG. 13A is a cross-sectional view of another exemplary embodiment of a socket sealing system of the present invention that is similar to the embodiment of FIG. 11A but includes an inner brim component instead of a soft inner socket.
Figure 13B:
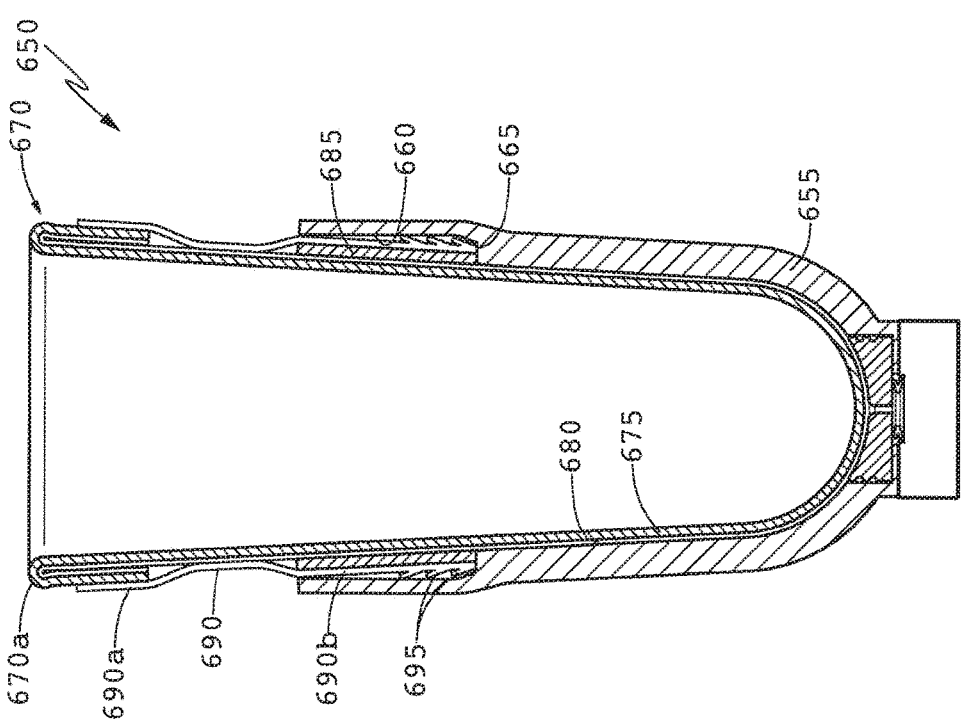
FIG. 13B is a cross-sectional view of another exemplary embodiment of a socket sealing system of the present invention that is similar to the embodiment of FIG. 13A but includes a separate sealing band.

Another exemplary embodiment of a socket sealing system (hereinafter "system") 650 of the present invention is depicted in FIGS. 13A and 13B. As shown, the system 650 includes a rigid outer prosthetic socket 655 having an open proximal end, a closed distal end, and an area of relief 660 along the interior of its proximal end that results in a peripheral shoulder 665 within the socket; and a polymeric prosthetic liner 670 for donning over an amputee's residual limb, the liner having an open proximal end, a closed distal end, a polymeric material interior 675 and an exterior fabric covering 680. In this embodiment, the soft inner socket of the previously described embodiment is replaced by a ring-like inner brim component 685 of regular or irregular peripheral shape that is designed to reside against the exterior of the prosthetic liner 670 within the relief area 660 of the rigid outer socket 655.

Also included is an open-ended polymeric sealing sleeve 690, the exterior of which may be partially covered with fabric (not shown). A distal portion 690b of the polymeric sealing sleeve 690 is arranged to reside within the relief area 660 of the rigid prosthetic socket 655, between the inner brim component 685 and the rigid prosthetic socket 655. The distal portion 690b of polymeric sealing sleeve 690 thus overlies and seals against the exterior of the inner brim component 685. A proximal portion 690a of the polymeric sealing sleeve 690 is designed to extend from the rigid prosthetic socket 655 and inner brim component 685 and to seal against a portion of the prosthetic liner 670 (or residual limb) that also extends from the rigid prosthetic socket and inner brim component In this embodiment, the open-ended sealing sleeve 690 again includes one or a plurality of substantially solid sealing elements 695 that are an integral part of and extend from the sealing sleeve along the area thereof that resides within the relief area 660 of the rigid prosthetic socket 655. The sealing elements 695 may again be as described above. The sealing elements 696 seal the exterior of the sealing sleeve 690 with the interior of the prosthetic socket 655.

As shown in FIG. 13B, the portion of the sealing sleeve 690 having sealing elements 695 that are an integral part thereof is replaced with a separate sealing band 700. Consequently, in this embodiment, the sealing band 700 includes sealing elements 705 and is designed to encircle and seal against the inner brim component 685 and to reside between the inner brim component and the rigid outer socket 655 in the relief area 660 thereof. The sealing elements 705 may again be as described above.

The sealing band 700 is employed to provide a seal between the inner brim component 685 and the rigid outer socket 655, and resides distally of the sealing sleeve 690. The sealing sleeve 690 functions as described above with respect to sealing against the prosthetic liner 670. In the particular exemplary embodiments shown in FIGS. 13A and 13B, the fabric covering 680 of the prosthetic liner 670 extends to the proximal end 670a thereof, and the proximal end is thus reflected as described previously such that the polymeric material 675 thereof is exposed and sealing of the liner 670 to the sleeve 690 is accomplished by overlapping the reflected proximal end 670a of the liner 670 with the proximal end 690a of the polymeric sealing sleeve 690.

Alternatively, the fabric covering 680 on the exterior of the prosthetic finer 670 may again terminate at some point before reaching the open end thereof (not shown), thereby leaving an exposed section of polymeric material 675 near the proximal end of the liner that extends beyond the rigid prosthetic socket 655 and soft inner socket 685. In this case, the polymeric material interior of the portion of the sealing sleeve 690 that also extends beyond the rigid prosthetic socket 655 and inner brim component 685 simply contacts and seals against the exposed polymeric material 675 of the liner 670.

Another exemplary embodiment of a socket sealing system (hereinafter "system") 750 of the present invention is depicted in FIGS. 14A and 14B. As shown, the system 750 includes a rigid outer prosthetic socket 755 having an open proximal end, a closed distal end, and an internal locking groove 760 of some shape located at some point between the distal and proximal ends thereof prosthetic liner; a polymeric prosthetic liner 765 for donning over an amputee's residual limb, the liner having an open proximal end, a closed distal end, a polymeric material interior 770 and an exterior fabric covering 775; and a soft inner socket 780 for receiving a portion of the liner-covered residual limb.

An open-ended polymeric sealing sleeve 785 is also used. The exterior of the sealing sleeve 785 may be partially covered with fabric (not shown). A distal portion of the sealing sleeve 785 is arranged to reside between the exterior of the soft inner socket 780 and the rigid prosthetic socket 755. A distal portion of polymeric sealing sleeve 780 thus overlies and seals against the exterior of the soft inner socket 780.

A distal end 785b of the polymeric sealing sleeve 780 is provided with a sealing and locking element 790 that extends circumferentially around and protrudes from the sealing sleeve, and is of a size, shape and location designed to enter and engage the internal locking groove 760 in the rigid prosthetic socket 755. In addition to performing a sealing function, the sealing and locking element 790 may assist with suspension in the case of vacuum failure. In another version of a prosthetic sealing sleeve that may be used with this system 750, the taper of the locking element 790 on the sealing sleeve 785 may be reversed.

The proximal end 785a of the sealing sleeve 785 extends beyond the open proximal end of both the soft inner socket 780 and rigid outer socket 755 to contact and seal against a portion of the prosthetic liner 765 that also extends beyond the open end of the soft inner socket and rigid outer socket.

As with previous embodiments, the proximal open end of the prosthetic liner 765 may be reflected or the liner may be provided with an area of exposed polymeric material against which the sealing sleeve 785 may seal.

Figure 15B:
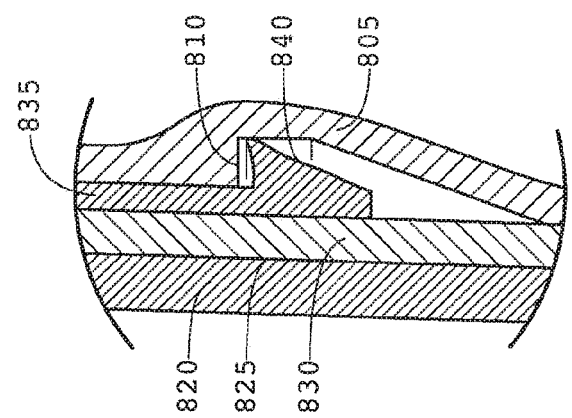
FIG. 15A and 15B illustrate another exemplary embodiment of a socket sealing system of the present invention, wherein a groove in a rigid socket engages a sealing element of a sealing sleeve.
Figure 15A:
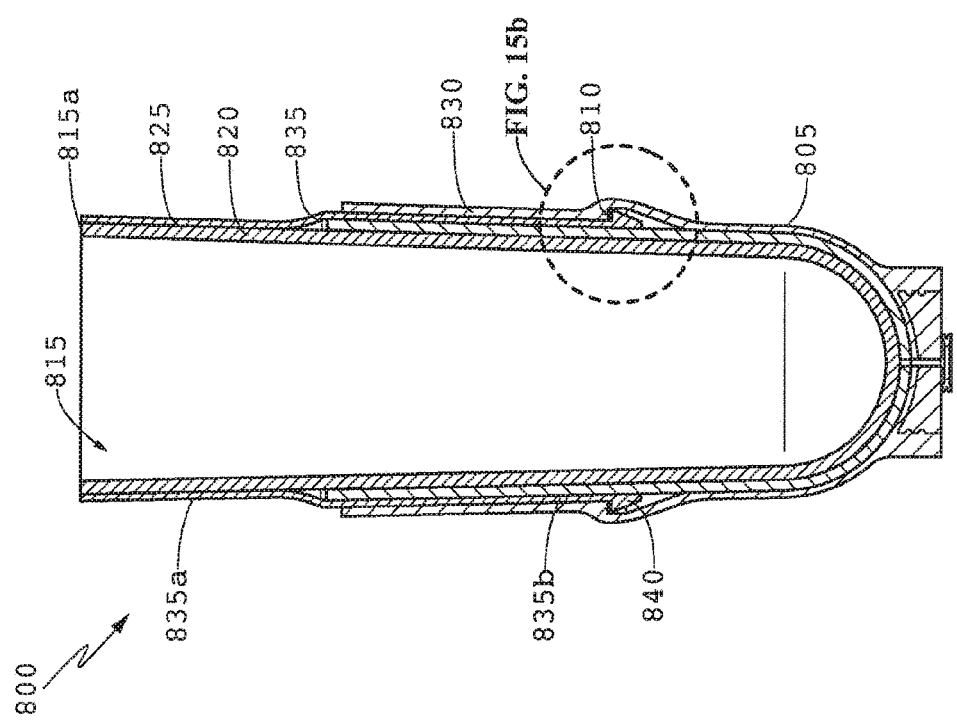

Another exemplary embodiment of a socket sealing system 800 is depicted in FIGS. 15A and 15B. As shown, system 800 includes a rigid outer prosthetic socket 805 having an open proximal end, a closed distal end, and an internal locking groove 810 located at some point between the distal and proximal ends thereof. In this embodiment, the locking groove 810 is preferably hook-shaped or half arrowhead-shaped at its proximal terminus. A polymeric prosthetic liner 815 for donning over an amputee's residual limb is provided, the liner having an open proximal end, a closed distal end, a polymeric material interior 820 and an exterior fabric covering 825. A soft inner socket 830 for receiving a portion of the liner-covered residual limb is also present.

An open-ended polymeric sealing sleeve 835 is also used. The exterior of the sealing sleeve 835 may be partially covered with fabric (not shown). A distal portion of the sealing sleeve 835 is arranged to reside between the exterior of the soft inner socket 830 and the rigid prosthetic socket 805. A distal portion of polymeric sealing sleeve 835 thus overlies and seals against the exterior of the soft inner socket 830.

A distal end 835b of the polymeric sealing sleeve 835 is provided with a sealing and locking element 840 that extends circumferentially around and protrudes from sealing sleeve 835, and is of a size, shape, and location that corresponds to internal locking groove 810 in rigid prosthetic socket 805. Thus, when sealing sleeve 835 is properly installed, sealing and locking element 840 not only provides a sealing function but may also assist with suspension in the case of vacuum failure. The shape of locking groove 810 and the shape of sealing and locking element 840 is able to account for a slight distal or proximal misalignment of the sealing and locking element 840 after initial donning, while also ensuring that the sealing and locking element 840 is forced into proper alignment with the locking groove once vacuum is applied.

The proximal end 835a of the sealing sleeve 835 extends beyond the open proximal end of both the soft inner socket 830 and rigid outer socket 805 to contact and seal against a portion of the prosthetic liner 815 that also extends beyond the open end of the soft inner socket and rigid outer socket. As with previous embodiments, the proximal open end 815a of the prosthetic liner 815 may be reflected or the liner may be provided with an area of exposed polymeric material against which the sealing sleeve 835 may seal.

Another exemplary embodiment of a sealing sleeve 850 of the present invention is depicted in FIGS. 16A-16C. The sealing sleeve 850 is shown in FIG. 16A to be a part of a sealing system 855 that includes a rigid outer prosthetic socket 860 having an open proximal end, a closed distal end, and an area of relief 865 along the interior of its proximal end that results in a peripheral shoulder 870 within the socket; a polymeric prosthetic liner 875 for donning over an amputee's residual limb, the liner having a polymeric material interior 880 and an exterior fabric covering 885 a soft inner socket 890 for receiving a portion of the liner-covered residual limb; and a polymeric sealing sleeve 900, the exterior of which may be partially covered with fabric (not shown).

A distal portion 900b of the polymeric sealing sleeve 900 is arranged to reside within the relief area 865 of the rigid prosthetic socket 860, between the soft inner socket 890 and the rigid prosthetic socket 860. The distal portion 900b of polymeric sealing sleeve 900 thus overlies and seals against the exterior of the soft inner socket 890. A proximal portion 900a of the polymeric sealing sleeve 900 is designed to extend from the rigid prosthetic socket 860 and soft inner socket 890 and to seal against a portion of the prosthetic liner 875 (or residual limb) that also extends from the rigid prosthetic socket.

Figure 17:
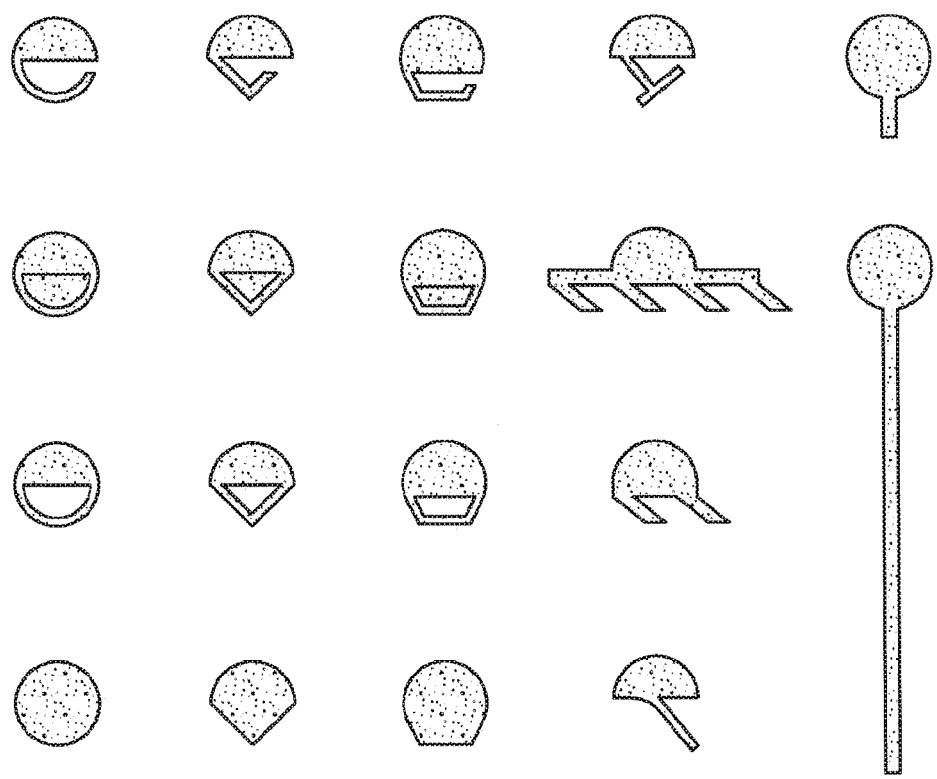
FIG. 17 depicts a multitude of non-limiting examples of sealing element shapes and designs.
Figure 18B:
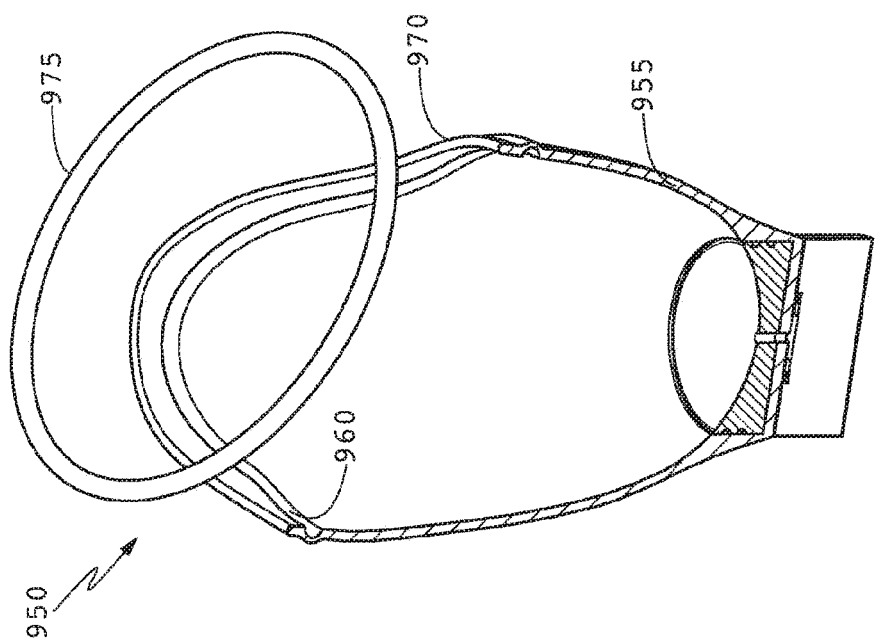
FIGS. 18A-18E illustrate another exemplary embodiment of a socket sealing system of the present invention.
Figure 18A:
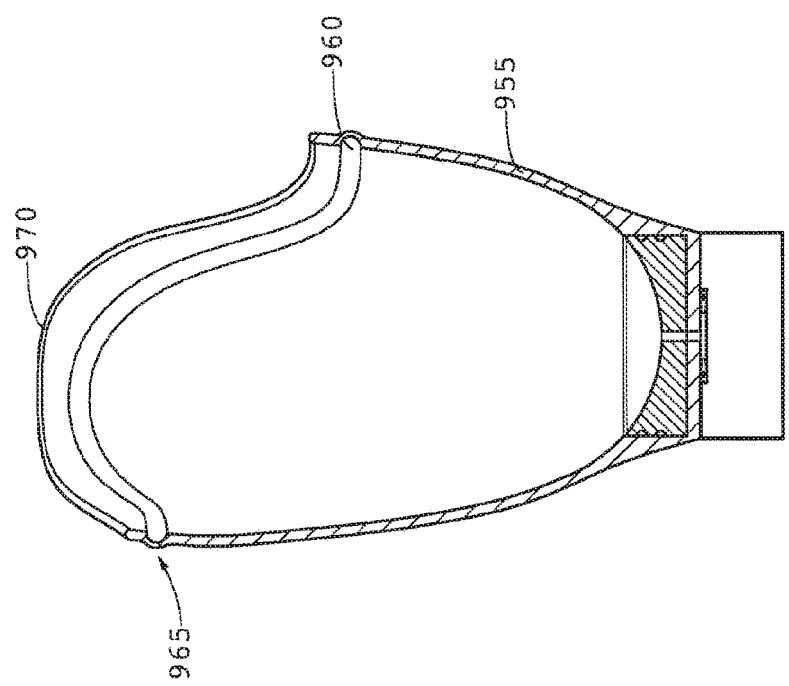
Figure 18D:
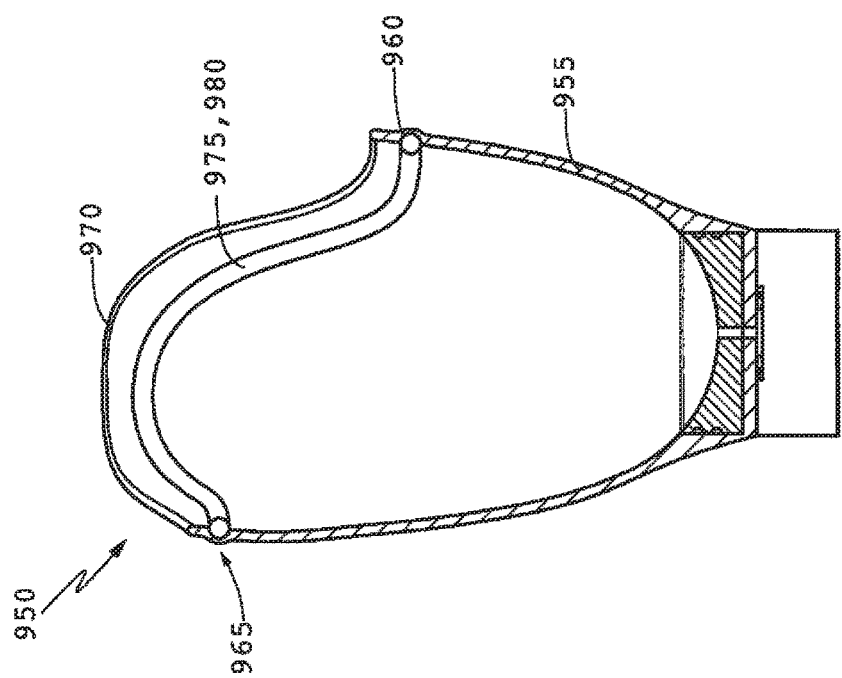
Figure 18C:
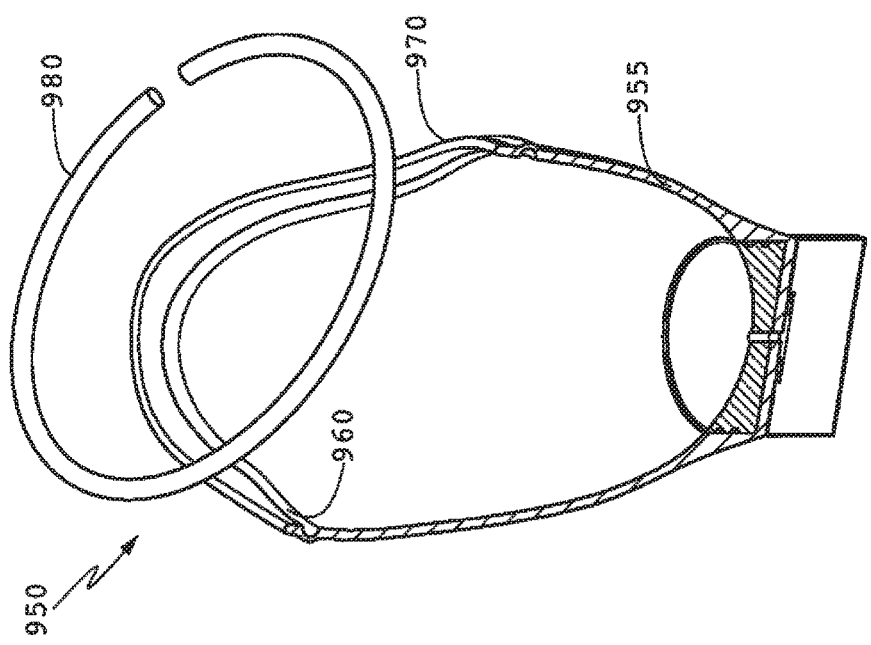
Figure 18E:
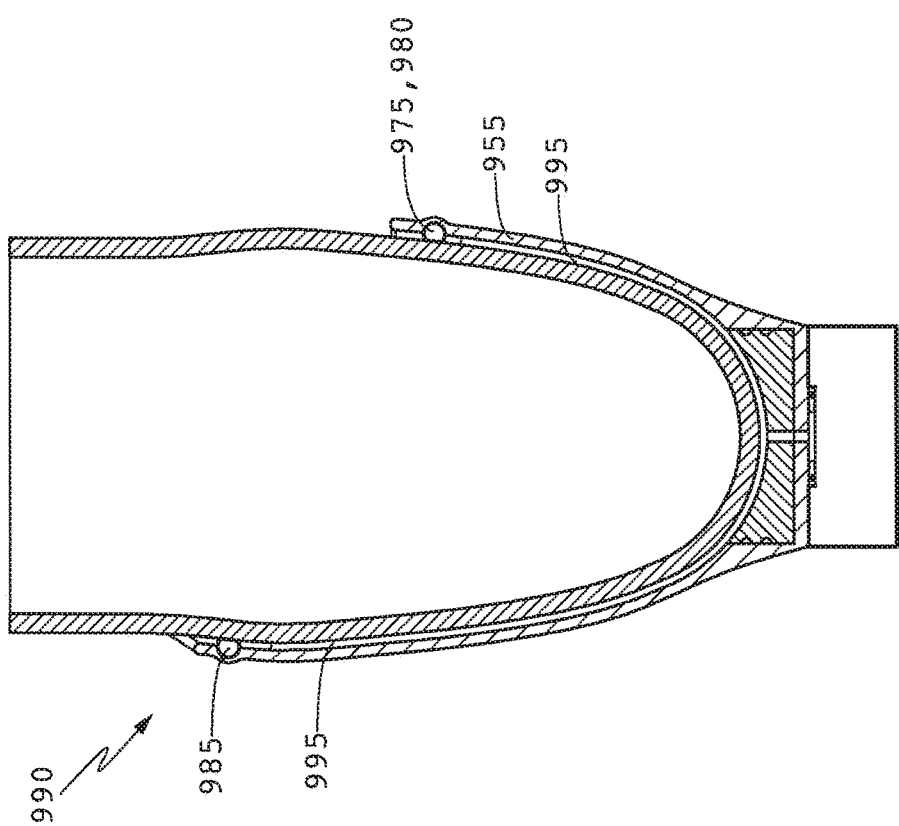

The sealing sleeve 850 demonstrates that in any of the aforementioned embodiments having a sealing sleeve or sealing band with one or more encircling sealing elements that are an integral part thereof, the substantially solid sealing elements may be replaced with one or more gas-filled bladders 895. The bladders 895 may be provided in a number of shapes, at least some of which are depicted in FIG. 17. The bladders 895 are again preferably devoid of a fabric covering so as to better seal against the interior of the prosthetic socket. In this case, sealing is assisted by the natural inflation of the bladders resulting from the pressure differential created when evacuation takes place.

FIG. 16B illustrates one exemplary manner in which a sealing sleeve 850 having gas-filled bladders 895 (air-filled, in this case) may be created. More specifically, an initial sleeve element 905 like that shown in FIG. 16B is first molded, which results in concave circumferential channels 910 being present on the exterior of the sleeve element. The portion of the sleeve element 905 containing the channels 910 is ten reflected over and bonded to an adjacent portion of the sleeve element, as shown in FIG. 16C, thereby creating a sealing sleeve 850 with a plurality of sealed bladders 895.

Various exemplary sealing element embodiments of different shapes and designs are depicted in FIG. 17. Such sealing elements may be used in, for example, the exemplary socket sealing systems illustrated in FIGS. 10A-13B and FIG. 16A.

Another exemplary embodiment of a socket sealing system (hereinafter "system") 950 of the present invention is depicted in FIGS. 18A-18E. As shown, the system 950 includes a rigid outer socket 955 having an internal and circumferentially-extending seal-receiving groove 960 located near the proximal open end 965 thereof and preferably substantially tracing the shape of the socket brim 970. A seal element 975, 980 is located within the seal-receiving groove 960 and adapted to protrude by some amount therefrom so as to seal against a prosthetic liner-covered residual limb 990 (see FIG. 18E) when the socket is worn by an amputee.

In this embodiment, the seal element 975, 980 is shown to be rod or rope-shaped, as is the corresponding seal-receiving groove 960. Other cross-sectional shapes may also be possible. The seal element 975, 980 is preferably comprised of a polymeric material such as silicone, and may have a central (axially-oriented) wire 985 running through all or a portion of its length. The wire 985 allows the seal element 975, 980 to retain bends that are imparted thereto, such as the bends that may be required to follow the shape of a prosthetic socket brim 970.

In use, the prosthetic socket 955 is sealed for vacuum suspension by contact of the seal element 975, 980 with the exterior of the prosthetic liner-covered residual limb 990. To this end, any fabric covering 995 on the exterior of the prosthetic liner either terminates at a point that is located distally of the seal element (see FIG. 18E), or an area of the fabric covering may be removed along the area of the seal element (not shown), such that the seal element is in contact with the polymeric material of the prosthetic liner.

In any of the aforementioned embodiments having a soft inner socket or an inner brim component, the proximal terminus thereof may, but is not necessarily required to, occur at approximately the same location as the proximal terminus of the rigid outer socket. Alternatively, it may be possible for one of the soft inner socket or inner brim component to extend proximally farther then the rigid outer socket, or vice versa.

All exemplary sealing system embodiments according to the invention may be used with a one-way valve in the case of passive vacuum suspension. Likewise, all exemplary sealing system embodiments according to the invention may be used with an evacuation system, which may include without limitation, a battery-powered vacuum pump. In this regard, the rigid outer sockets of embodiments of the invention may be equipped with internal adapters and/or other components that facilitate vacuum suspension. When a soft inner socket is used, the distal end of the soft socket may be modified to have an opening via which vacuum can be applied to the liner-covered residual limb. When a sealing sleeve having a closed end is placed over a soft inner socket, it may be similarly modified.

FIG. 19 illustrates several non-limiting examples of other vacuum-related components that may be used with a socket sealing system of the present invention. For example, a socket sealing system of the present invention may include a vacuum device (e.g., vacuum pump and power source) 250 that may be attached to the prosthetic socket at various locations. Such a vacuum device 250 may be provided with onboard pressure and/or motion sensing capabilities. In this particular embodiment, the vacuum device 250 is connected to an air bypass valve 255 by a vacuum line 260. The air bypass valve includes a push-button air release 260. Sensors 265, 270 may also be located in a socket and/or liner, respectively, and may be used to detect and report various conditions associated with the vacuum suspension of a prosthesis or with other conditions of a prosthesis or an amputee's residual limb. It is also contemplated that the material of the socket and/or the fabric and/or polymeric material of the liner may be thermally conductive.

While certain embodiments of the present invention are described in detail above, it is to be realized that other combinations of elements not specifically shown or described here are certainly possible. For example, the exemplary embodiments shown and described herein as having a sealing sleeve with sealing elements being an integral part thereof may instead include a sealing sleeve without such sealing elements. Consequently, the scope of the invention is not to be considered limited by the disclosure of exemplary embodiments made herein, and modifications are possible without departing from the spirit of the invention as evidenced by the following claims:

What is claimed is:

1. An apparatus comprising:
   a prosthetic socket having an open proximal end configured for insertion of a residual limb, a distal end configured to reach across a distal end of the residual limb, a peripheral shoulder within the socket, a first interior periphery reaching from the shoulder to the distal end, and a second interior periphery reaching from the shoulder to the open proximal end, wherein the second interior periphery is enlarged relative to the first interior periphery to define a receiving section of the socket having a depth that is recessed outwardly from the first interior periphery to the second interior periphery;
   a sealing sleeve received within the receiving section of the socket, the sealing sleeve having a distal end within the receiving section of the socket between the shoulder and the open proximal end of the socket; and
   a ring-shaped inner brim received within the receiving section of the socket between the residual limb and the sealing sleeve, the inner brim having both a proximal end and a distal end within the receiving section of the socket between the shoulder and the open proximal end of the socket, and having a thickness less than the depth of the receiving section, whereby the inner brim is contained entirely within the receiving area of the socket and seals the sealing sleeve against the socket within the receiving section of the socket.

2. An apparatus as defined in claim 1 wherein the sealing sleeve has a proximal portion extending from the receiving section of the socket outward past the proximal end of the inner brim.

3. An apparatus as defined in claim 1 further comprising a liner having an open proximal end configured for insertion of the residual limb into the liner, and having a distal end configured to reach across a distal end of the residual limb, wherein the inner brim is received within the receiving section of the socket between the liner and the sealing sleeve.

4. An apparatus as defined in claim 1 wherein the liner has a proximal portion extending outward from the open proximal end of the socket past the proximal end of the inner brim.

5. An apparatus as defined in claim 4 wherein the sealing sleeve has a proximal portion extending outward from the enlarged interior periphery of the socket, and the proximal portion of the sealing sleeve overlies the proximal portion of the liner.

6. An apparatus as defined in claim 1 wherein the thickness of the inner brim is uniform between the proximal end and the distal end.

* * * * *